(12) United States Patent
Kvernebo

(10) Patent No.: US 10,987,011 B2
(45) Date of Patent: Apr. 27, 2021

(54) ASSESSING CIRCULATORY FAILURE

(71) Applicant: Oslo Universitetssykehus HF, Oslo (NO)

(72) Inventor: Knut Kvernebo, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 0 days.

(21) Appl. No.: 14/763,872

(22) PCT Filed: Jan. 28, 2014

(86) PCT No.: PCT/EP2014/051661
§ 371 (c)(1),
(2) Date: Jul. 28, 2015

(87) PCT Pub. No.: WO2014/114814
PCT Pub. Date: Jul. 31, 2014

(65) Prior Publication Data
US 2015/0359440 A1  Dec. 17, 2015

(30) Foreign Application Priority Data

Jan. 28, 2013 (GB) ..................................... 1301490
Jul. 17, 2013 (GB) ..................................... 1312796

(51) Int. Cl.
*A61B 5/00* (2006.01)
*A61B 5/026* (2006.01)
(Continued)

(52) U.S. Cl.
CPC .............. *A61B 5/0261* (2013.01); *A61B 3/13* (2013.01); *A61B 5/0075* (2013.01);
(Continued)

(58) Field of Classification Search
CPC ....... A61B 5/0261; A61B 5/13; A61B 5/0075; A61B 5/0077; A61B 5/2007;
(Continued)

(56) References Cited

U.S. PATENT DOCUMENTS 5,507,287 A * 4/1996 Palcic ................ A61B 1/00186
356/318
5,553,613 A * 9/1996 Parker ................ A61B 5/14532
600/316
(Continued)

FOREIGN PATENT DOCUMENTS

JP  2006325714 A  12/2006
JP  2007516009 A  6/2007
(Continued)

OTHER PUBLICATIONS

Joakim Henricson, "Assessment of microvascular effects of vasoactive drugs" Linkoping University (Year: 2009).*
(Continued)

*Primary Examiner* — Joanne M Hoffman
(74) *Attorney, Agent, or Firm* — Meunier Carlin & Curfman LLC

(57) ABSTRACT

The present invention relates to a method of identifying or monitoring circulatory failure in a subject, which method comprises assessing the subject's microcirculation in respect of the following parameters: (a) functional capillary density (FCD); (b) heterogeneity of the FCD; (c) capillary flow velocity; (d) heterogeneity of capillary flow velocity; (e) oxygen saturation of microvascular erythrocytes ($SmvO_2$); and (f) heterogeneity of $SmvO_2$; wherein parameters (a) to (d) are assessed visually by microscopy and parameters (e) and (f) are assessed by diffuse reflectance spectroscopy (DRS); well as apparatus and software designed for performance of such a method.

12 Claims, 8 Drawing Sheets

(51) Int. Cl.
    *A61B 5/1455*     (2006.01)
    *A61B 3/13*     (2006.01)
    *A61B 5/02*     (2006.01)
    *A61B 5/0205*     (2006.01)
    *A61B 5/1464*     (2006.01)

(52) U.S. Cl.
    CPC .......... *A61B 5/0077* (2013.01); *A61B 5/0205* (2013.01); *A61B 5/02007* (2013.01); *A61B 5/14551* (2013.01); *A61B 5/14552* (2013.01); *A61B 5/14558* (2013.01); *A61B 5/445* (2013.01); *A61B 5/489* (2013.01); *A61B 5/4848* (2013.01); *A61B 5/1464* (2013.01); *A61B 2503/045* (2013.01); *A61B 2505/03* (2013.01); *A61B 2576/00* (2013.01)

(58) Field of Classification Search
    CPC .............. A61B 5/0205; A61B 5/14551; A61B 5/14552; A61B 5/445; A61B 5/4848; A61B 5/489
    See application file for complete search history.

(56) References Cited

U.S. PATENT DOCUMENTS

| | | | | |
|---|---|---|---|---|
| 5,699,797 | A * | 12/1997 | Godik | A61B 5/0261 600/407 |
| 5,713,364 | A * | 2/1998 | DeBaryshe | A61B 1/00059 250/461.2 |
| 5,769,792 | A * | 6/1998 | Palcic | A61B 5/0071 356/318 |
| 6,104,945 | A * | 8/2000 | Modell | A61B 1/00059 250/461.2 |
| 6,377,841 | B1 * | 4/2002 | Lin | A61B 5/0059 356/303 |
| 6,420,709 | B1 * | 7/2002 | Block | A61B 5/14532 250/343 |
| 8,214,023 | B2 * | 7/2012 | Fymat | A61B 5/0059 250/341.1 |
| 2001/0041843 | A1 * | 11/2001 | Modell | A61B 5/0066 600/473 |
| 2002/0007122 | A1 * | 1/2002 | Kaufman | A61B 1/00009 600/476 |
| 2002/0161282 | A1 * | 10/2002 | Fulghum | A61B 1/00009 600/160 |
| 2002/0165456 | A1 * | 11/2002 | Canpolat | A61B 5/0059 600/473 |
| 2003/0135092 | A1 * | 7/2003 | Cline | A61B 1/00009 600/160 |
| 2005/0154319 | A1 * | 7/2005 | Cline | A61B 1/00009 600/478 |
| 2005/0240107 | A1 * | 10/2005 | Alfano | A61B 5/0059 600/476 |
| 2006/0241364 | A1 * | 10/2006 | Ince | A61B 5/0261 600/323 |
| 2009/0012378 | A1 | 1/2009 | Ince | |
| 2010/0185064 | A1 * | 7/2010 | Bandic | A61B 5/0059 600/306 |
| 2012/0326055 | A1 * | 12/2012 | Wilson | A61B 5/0059 250/459.1 |

FOREIGN PATENT DOCUMENTS

| | | |
|---|---|---|
| JP | 2008522185 A | 6/2008 |
| JP | 2012205855 A | 10/2012 |
| WO | 201153521 A2 | 12/2011 |

OTHER PUBLICATIONS

Alba-Alejandre, et al., "Microcirculatory Changes in Term Newborns with Suspected Infection: An Observational Prospective Study", International Journal of Pediatrics, 2013, Article ID 768784.

Arnold R. C. et al., "Point of care assessment of microvascular blood flow in critically ill patients", Intensive Care Med, 35(10), 2009, 1761-6.

Awan, Z. A. et al., "Diffuse reflectance spectroscopy: systemic an microvascular oxygen saturation is linearly correlated and hypoxia leads to increased spatial heterogeneity of microvascular circulation", Microvascular Research, 81, 2011, 245-251.

Awan, Z. A. et al., "Human microvascular imaging: a review of skin and tongue videomicroscopy techniques and analysing variables", Clin Physiol Funct Imaging, 30, 2010, 79-88.

Backer et al., "Monitoring the microcirculation in the critically ill patient: current methods and future approaches", Intensive Care Medicine 36(11), 2010, 1813-1825.

Bezemer, R. et al., "Clinical review: Clinical imaging of the sublingual microcirculation in the critically ill—where do we stand? ", Crit Care. 16(3), 2012, 224.

Bezemer, R. et al., "Rapid autonomic assessment of microvascular density in sidestream darkfield images", Med Biol Eng Comput. 49(11), 2011, 1269-1278.

Corstiaan, A. "Impaired microcirculation predicts poor outcome of patients with acute myocardial infarction complicated by cardiogenic shock", 31, 2010, 3032-3039.

De Backer, D. et al., "Microvascular blood flow is altered in patients with sepsis", Am J Respir Crit Care Med, 166(1), 2002, 98-104.

Demir S. U. et al., "An automated method for analysis of microcirculation videos for accurate assessment of tissue perfusion", BMC Med Imaging. 12(37), 2012.

Dobbe, J. G. G. et al., "Measurement of functional microcirculatory geometry and velocity distributions using automated image analysis", Med Biol Eng Comput. 46(7), 2008, 659-670.

Dublin, A. "Microcirculation in the intensive care unit", Rev Bras Ter Intensive, 23(3), 2011, 249-251.

Ferrell, et al., "A diffusion theory model of spatially resolved, steady-state diffuse reflectance for the noninvasive determination of tissue optical properties in vivo," The American Association of Physicists in Medicine, 19(4), 1992, pp. 879-888.

Genzel-Boroviczény, O. et al., "Blood transfusion increases functional capillary density in the skin of anemic pre-term infants", Pediatr Res., 56(5), 2004, 751-5.

Goedhart, P. T. et al., "Sidestream dark field (SDF) imaging: a novel stroboscopic LED ring-based imaging modality for clinical assessment of the microcirculation", Optics Express, 15(23), 2007, 15101-15114.

Green, D. J. et al., "Impaired skin blood flow response to environmental heating in chronic heart failure", European Heart Journal, 27, 2006, 338-343.

Hale, el al., "Optical Constants of Water in the 200-nm to 200-um Wavelength Region", Appl. Opt.12, 1973, 555-63.

Iakovlev, V. V. et al., "Microvascular density as in independent predictor of clinical outcome in renal cell carcinoma: an automated image analysis study" Lab Invest. 92(1), 2012, 46-56.

International Preliminary Report on Patentability and Written Opinion, dated Jul. 28, 2015, received in connection with International Patent Application No. PCT/EP2014/051661.

International Search Report, dated Apr. 3, 2014, received in connection with International Patent Application No. PCT/EP2014/051661.

Jacques, J.L., "Time-resolved reflectance spectroscopy in turbid tissues," IEEE Transactions on Biomedical Engineering, vol. 36, No. 12, 1989, pp. 1155-1161.

Klijn, E. et al., "The heterogeneity of the microcirculation in critical illness", Clin Chest Med., 29, 2008, 643-654.

Krohg-Sørensen, K. et al., "Laser Doppler flux and tissue oxygenation tension as indicators of colonic perfusion in pigs", 159, 1993, 293-299.

Kroth, J. et al., "Functional vessel density in the first month of life in pre-term neonates", Pediatric Research, 64(5), 2008, 567-570.

Line, P. D. et al., "Repeated measurement variation and precision of laser Doppler flowmetry measurements", Microvascular Research, 43, 1992, 285-293.

Meglinsky, et al., Modelling the sampling volume for skin blood oxygenation measurements 10 Med Biol Eng Comput 39(1), 2001, 44-50.

(56) References Cited

OTHER PUBLICATIONS

Mertz, M. D. et al., "Automated immunofluorescence analysis defines microvessel area as a prognostic parameter in clear cell renal cell cancer", Human Pathology, 38, 2007, 1454-1462.

Mørk, C. et al., "Reduced skin capillary density during attacks or erythromyalgia implies arteriovenous shunting as pathogenetic mechanism" Journal of Investigative Dermatology, 119(4), 2002, 950-953.

The Microscan Instrument, Microvision Medical, Aug. 5, 2011.

Top, A. P. et al., "Persistent low microcirculatory vessel density in non-survivors of sepsis in pediatric intensive care", Crit Care Med. 31(1), 2011, 8-13.

Trzeciak, S. et al., "Early microcirculatory perfusion derangements in patients with severe sepsis and septic shock: relationship to hemodynamics, oxygen transport and survival", Annals of Emergency Medicine, 49(1), 2007, 88-98.

Wester, T. et al., "Assessment of skin and tongue microcirculation reveals major changes in porcine sepsis", Clin. Physiol. Funct. Imaging, 31, 2011, 151-158.

Zhao, M. Y. et al., "The Clinical significance of determining the severity and prognosis by monitoring the Changes in sublingual microcirculation in patients with severe sepsis", Zhongguo Wei Zhong Bing Ji Jiu Yi Xue, 24(3), 2012, 158-161.

\* cited by examiner a)

b)

ASSESSING CIRCULATORY FAILURE

The present invention relates to the analysis of the microcirculation of a subject, and in particular to methods of, and apparatus for, such analysis and to the use of data obtained thereby. For example, data obtained by means of the present invention may be used to assess the prognosis of subjects presenting with symptoms of circulatory failure, and to assess the effects of treatment of circulatory failure in a patent. The methods of the invention can also provide an early warning of circulatory problems prior to a clinical diagnosis thereof.

Circulatory failure can be defined as the inability of the cardiovascular system to supply sufficient amounts of oxygen to meet the metabolic demands of the cells of the body. In clinical medicine, unfortunately, there is no gold standard for monitoring of tissue oxygenation. (Arnaldo Dubin. Rev Bras Ter Intensiva. 2011; 23(3):249-251)

Since the circulation of blood refers to its continual flow from the left side of the heart, through branching arteries, to reach and traverse the microscopic vessels in all parts of the body, returning via the veins to the right side of the heart, to flow on through the lungs and back to the left heart again, disease processes in the heart, the lungs and the transport vessels, as well as in the microcirculation can cause circulatory failure. These conditions may develop acutely or over time. Lack of oxygen delivery may lead to cellular dysfunction or death, and may proceed to organ failure and death of an individual. Circulatory failure can be local or systemic. Generalized (i.e. systemic) and clinically evident failure, i.e. shock, may be central (e.g. caused by heart failure or hypervolemia) or peripheral (e.g. distributive failure caused by sepsis).

Economic consequences of circulatory failure are large but difficult to calculate. It would be of great benefit if available resources could be allocated to patients with the best overall chance of survival.

For example, acute cardiac heart failure compromises central hemodynamics and consequently microvascular perfusion throughout the body. The mortality rate varies from 50 to 80 percent. Veno-arterial extra-corporeal membrane oxygenation (va-ECMO) may be used as a bridge to recovery or to other destination therapy. However, only approximately one-third of adult patients treated on ECMO for cardiogenic shock survive. ECMO treatment is resource-demanding and the assumption underlying its use, that improved technological solutions and central hemodynamics—i.e. improved blood pressure and cardiac output—translates into improved survival, may not be completely valid. Mortality in ECMO patients is most often caused by sepsis, multi-organ failure or bleeding complications.

As well as systemic circulatory failure which may threaten life, there may be localised circulatory failure (which may itself be life threatening, for example, if the organ affected is essential or if the affected region could become necrosed and result in sepsis) such as erythromelalgia. No reliable and accepted parameter or set of parameters have been established to assess the microcirculation and make clinical decisions on the data generated.

Clinical examination of arterial and venous circulation may give valuable information, but conclusions are often wrongly extrapolated to be valid for conclusions of microvascular function. A large number of technologies, like blood gas analyses and assessment of metabolic products in blood samples, pressure- and cardiac output measurements, as well as imaging techniques, are used to diagnose and guide treatment of circulatory failure. These techniques collect data assessing function of the heart, veins and arteries, as well an average index of the metabolic function of the body. However the same problem applies to these measurements as to clinical assessments: measured values within the reference spectrum can coexist with critical systemic or local circulatory failure.

The challenge is therefore to improve technologies to measure reproducible and relevant microvascular parameters that can be used to assess oxygen delivery to the cells, because if this delivery fails, cells will not function and eventually die.

A myriad of different parameters and measuring techniques for diagnosing and assessing circulatory failure exist, as mentioned above. These may include blood tests, for example to determine acid-base balance in arterial blood or levels of lactate in serum. Arterial and venous circulation may be measured: here techniques include imaging using contrast media (angiography, venography and magnetic resonance (MR) assessments); Doppler ultrasound measurements of blood flow velocities; and invasive and non-invasive blood pressure measurements.

Tissue perfusion may be assessed, for example through isotope washout, Doppler ultrasound or laser Doppler (LD). There are various metabolic parameters which can also be measured, such as oxygen saturation in the muscle or brain using near infrared spectroscopy or transcutaneous diffusion of oxygen or $CO_2$.

Microscopic techniques to view the microcirculation include orthogonal polarization spectral (OPS) imaging, sidestream dark field (SDF) imaging and computer assisted video microscopy (CAVM). OPS and SDF are of limited utility as they cannot be used to generate quality images from adult skin, only the tongue and possibly the conjunctiva. CAVM allows real time examination of microvessels so that their morphology, capillary structure and flow patterns can be studied.

From amongst this array of possible parameters and measuring techniques, Dubin (supra) concludes that a suitable approach may be to use (i) sublingual SDF imaging, (ii) muscle $AStO_2$ (the slope of the recovery of muscle oxygen saturation after an occlusion test) and tissue capriometry.

Wester et al. in Clin. Physiol. Funct. Imaging (2011) 31, pp 151-158 use a combination of CAVM and LD in their assessment of the microcirculation in porcine sepsis and also reported the value of analysing pericapillary bleedings.

Klijn et al. in Clin. Chest Med. (2008) 29, pp 643-654 focus on OPS and SDF in their discussion of critical illness studies of the microcirculation.

Awan et al. in Microvascular Research (2011) 81, pp 245-251 describe the use of diffuse reflectance spectroscopy (DRS), which enables the oxygen saturation of the erythrocytes located in microvessels to be measured.

The field does not lack parameters or tools to investigate circulatory failure but lacks a reliable test or framework to assess systemic or localised circulatory failure, preferably one that is appropriate for many patient groups and clinical scenarios. There is no accepted standard and data can conflict.

The present inventors have developed a method of analysing and evaluating circulatory failure or possible circulatory failure which relies on six key parameters. These parameters, taken together, are surprisingly effective at predicting clinical outcome, in particular in determining whether a subject has circulatory failure and whether, in severe cases, their chances of survival are good or not. It is also of utility in assessing localised circulatory failure.

Thus, in one aspect, the present invention provides a method of identifying or monitoring circulatory failure in a subject, which method comprises assessing the subject's microcirculation in respect of the following parameters:
(a) functional capillary density (FCD);
(b) heterogeneity of the FCD;
(c) capillary flow velocity;
(d) heterogeneity of capillary flow velocity;
(e) oxygen saturation of microvascular erythrocytes ($SmvO_2$); and
(f) heterogeneity of $SmvO_2$;
wherein parameters (a) to (d) are assessed visually by microscopy and parameters (e) and (f) are assessed by diffuse reflectance spectroscopy (DRS).

"Circulatory failure" does not imply total failure, but the insufficient delivery of oxygen and nutrients to the organs and cells of the body, usually in spite of full oxygen saturation of erythrocytes in the arteries. Circulatory failure can be defined as the inability of the cardiovascular system to supply sufficient oxygen to meet the metabolic demands of the cells of the body.

The "microvasculature" or "microcirculation" include the capillaries, metarterioles, sinusoids and venules.

Circulatory failure may be systemic or localised and the invention is particularly suitable and useful for identifying systemic circulatory failure. Localised failure means that it does not affect all (or substantially all) cells of the body.

Examples of localised failure or potential failure include limb ischaemia, erythromelalgia, wounds, Reynaud's syndrome, psoriasis, allergic inflammation of the retina, failure associated with organ transplant (not the heart). Systemic failure may be due, inter alia, to sepsis, malaria, cardiogenic shock or bleeding after trauma (hypovolemia). Long standing diabetes mellitus may also be accompanied by systemic circulatory failure.

Assessment of the microcirculation includes analysis of the microvascular morphology and physiology, in particular to assess the capability of the microcirculation to deliver oxygen and/or nutrition to the surrounding cells. Thus, the invention is based on the hypothesis that pathological microvascular morphology and physiology correlates to a poor prognosis and specifically to circulatory failure, particularly to life threatening circulatory failure. Therefore the results of these microvascular examinations can be used to improve selection of appropriate treatment and/or to guide or monitor therapy. Using trend analyses from repeated assessments taken before and after start of a specific treatment for identified circulatory failure the responders to the treatment can be identified and in non-responders the treatment can be stopped. In this way subjects who benefit from ECLS (Extra corporeal life support (this includes ECMO) may be identified.

Thus, the present invention can also provide "stop criteria" for when to withdraw a certain treatment, in particular a life support treatment.

The examination of the microcirculation need only relate to localised area(s) of the subject since, in the case of a subject with systemic circulation failure, the local state of the microcirculation is considered to provide a good indication of the systemic microcirculation. Nevertheless, assessments may be made in relation to multiple areas.

Assessment of the microcirculation may also comprise analysis of pericapillary pathology, such as determining whether pericapillary bleedings and/or dark haloes are visible.

The invention may conveniently be performed by analysing the microcirculation of the skin. However, data may also be obtained from the microcirculation of any accessible microvascular bed, for example, sublingual or from the microcirculation in the conjunctiva. The skin may, but preferably does not, include the nail fold.

In certain embodiments the body or a region thereof has experienced hypoxia and the method of the invention serves to investigate whether the hypoxia caused by a period of circulatory failure has resulted in irreversible damage, for example in the case of limb ischaemia. Different tissues can cope with different periods of hypoxia, with nerves the most sensitive. Although damage to the nerves may be the limiting factor, according to the present invention it is not necessary to monitor the nerves, analysis of the microvasculature, e.g. of the skin, can give relevant clinical, e.g. prognostic information, including whether reperfusion of a damaged limb has been successful.

The visual assessment of the microcirculation comprises the use of a microscope to provide images, and preferably to the use of a video microscope, and/or the use of images (still and/or moving) obtained by (video) microscopy. The microscope is preferably digital and is preferably computer assisted video microscopy (CAVM).

The microscope preferably uses unpolarised light. The microscope preferably uses polychromatic light, e.g. white light, such as produced by a conventional microscope light source.

Films and single frames (images) may be analysed offline, if necessary, remotely from the patient. (Here "off-line" means without the microscope being in contact with or connected to the subject, e.g. after the completion of the gathering of the images). Thus in certain embodiments, the methods of the invention comprise assessing the subject's microcirculation through the analysis of (video)-microscopy images thereof.

The present invention also provides a method of identifying or monitoring circulatory failure in a subject, which method comprises assessing the subject's microcirculation visually by analysis of images thereof obtained using a microscope (parameters (a)-(d) as described herein) and by analysis of spectra obtained by DRS performed on the microvessels of the subject. DRS spectra provide information about the amount of oxy- and deoxy-haemoglobin in the microvessels. This information can be used to estimate oxygen saturation of erythrocytes within the microvessels.

The images are preferably obtained by applying the video microscope gently to the surface of the skin (or other tissue like the tongue or the conjunctiva of the eye), preferably using immersion oil, with the images being transmitted to a computer for storage, i.e. preferably computer-assisted video microscopy (CAVM) is employed.

The methods of the invention may provide an early indication of circulatory failure. Alternatively, for subjects who are believed to have some degree of circulatory failure, the techniques can be used prognostically.

Thus, viewed from a further aspect, the invention provides a method of making a prognosis for a subject with circulatory failure, the method comprising assessing the subject's microcirculation in respect of the following parameters:
(a) functional capillary density (FCD);
(b) heterogeneity of the FCD;
(c) capillary flow velocity;
(d) heterogeneity of capillary flow velocity;
(e) oxygen saturation of microvascular erythrocytes ($SmvO_2$); and
(f) heterogeneity of $SmvO_2$;

wherein parameters (a) to (d) are assessed visually by microscopy and parameters (e) and (f) are assessed by diffuse reflectance spectroscopy (DRS).

Where the results of the investigations indicate a severe disturbance in the microcirculation (i.e. a large deviation from a healthy microcirculation), then the subject can be given all possible interventions as part of Intensive Care therapy. The care response is selected to match the prognosis provided by the method of the invention.

Pathological microvascular morphology and/or perfusion correlate to poor prognosis, with the prognosis becoming worse as the degree of pathology increases. If desired, the degree of pathology may be quantified by comparison to the microcirculation of healthy subjects and determining the degree of deviation. Likewise circulatory failure can be identified, and the severity thereof established, through observation of a pathological microcirculation and the degree of deviation from a healthy microcirculation.

Analysis of images obtained by microscopy may comprise selecting one or more images based on pre-determined criteria (e.g. to ensure suitable quality) and optionally applying a grid to facilitate analysis.

As noted above, the results of analysis may be quantified by comparison to reference values based upon values obtained from corresponding examinations of healthy subjects, with a significant deviation from those values being indicative of circulatory failure. Those reference values may be generated as described in the Examples herein. Preferably test results can be compared against a database of reference values or against threshold values obtained from a database. Such a database may include healthy reference values and values from subjects determined to have or have had circulatory failure.

Circulatory failure may be identified or a poor prognosis given even if only 1 or 2 of the parameters (a)-(f) are outside reference values. Generally, the more parameters that fall outside healthy reference values the worse the prognosis or the more severe the circulatory failure or the longer the period of hypoxia.

Where pericapillary bleedings and/or dark haloes are present, the number per unit area and/or proportion of capillaries affected may be calculated.

FCD may, at least in relation to skin-based measurements, be defined as the number of visible capillary loops per unit area, e.g. per square millimetre, or if capillaries are organised parallel to the tissue surface, the number of capillaries crossing a grid of lines per mm line. For example, subjects with a FCD below 8 crossings/mm line in a grid of lines are likely to have circulatory failure, when measurements are done in areas where the microvessels are parallel to the tissue surface. Values above 9 crossings/mm indicate a good prognosis.

If assessments are done in skin where only nutritional papillary loops are seen, the prognosis is severe (circulatory failure is indicated) with less than 55 (worse with less than 50) visible loops/mm$^3$, and values above about 60 (e.g. 58-75) loops/mm$^3$ indicate a good prognosis. These values apply to all ages and clinical settings and refer to the number of loops seen from the surface of the skin, where the loops are perpendicular to the skin surface.

The capillary density is "functional" in that the measured capillaries are observed to contain erythrocytes.

FCD is preferably provided as a mean value, e.g. based on 4 to 20, more preferably 5-10, most preferably 7-10 repeated measurements. Thus according to the methods of the invention several images or video sequences are obtained and the FCD of each determined before a mean is calculated.

Heterogeneity as determined according to parameters (b), (d) and (f) is an indication of the variation seen between multiple values. In general, larger variations are a bad sign. Heterogeneity is preferably found by determining the coefficient of variance over a plurality of different locations in the same area (the coefficient of variance—CoV—is the standard deviation divided by the mean). These are most conveniently provided by analysing a plurality of images of randomly selected areas of the skin.

Neonates with a CoV for FCD above 0.35 are likely to have circulatory failure, with healthy values lying below 0.35. For adult patients (e.g. those undergoing or being considered for intensive care therapy), those with a CoV for FCD above 0.38 have a poor prognosis/are likely to have circulatory failure, with ideal values lying within the range of 0.15 to 0.3.

Heterogeneity preferably depends on analysis of at least 4 images, preferably 5-10 images, e.g. 6-8 images.

Line et al (1992) in Microvascular Research, 43, pp 285-293 describe (in the context of LD flowmetry measurements) how the number of samples required to provide a reliable mean and heterogeneity score may be derived.

Blood capillary flow velocity (CFV) may be measured for each of a plurality of microvessels. It is sufficient for velocity to be estimated based on a number of categories. For example, there may be five categories, which may be assessed visually: 0=no flow; 1=sluggish flow (very slow cell movement, sometimes backward flow); 2=continuous low flow (cells moving continuously forward, mostly slowly); 3=continuous high flow (cells moving continuously forward, mostly rapidly); 4=brisk flow (rapidly moving cells throughout the entire film sequence). Brisk flow relates to a flow rate significantly higher than normal which results in poor perfusion as the oxygen carried by the erythrocytes in such microvessels does not stay long enough in the microvessel to be delivered to the tissue. Such microvessels will act as a physiological arterio-venous shunt.

Preferably a mean flow-categorical velocity is determined. The mean flow-categorical velocity (MFCV) may be determined for the capillaries on a given set of images, by the following formula: Mean flow-categorical velocity={Fr (1)×1}+{Fr (2)×2}+{Fr (3)×3}+{Fr (4)×4}, where Fr stands for the fraction of capillaries within each flow category. Such a calculation is described by Wester et al., supra.

As an alternative to the MFCV value, capillary flow velocity may be assessed in terms of the number or proportion of capillaries categorised as 0 or 1 or 0 or 4 (negative sign when proportion is high) or the number or proportion categorised as 2 or 3 (positive when high).

An optimal distribution of capillary flow velocities and low variation of flow velocities among capillaries (both as compared to healthy controls) generally correlate to good circulatory function. Ideally there should be 20-30% in category 2 and 70-80% in category 3, and 95% in categories 2 and 3 combined. The best prognosis arises when the figures are closest to 25% in category 2 and 75% in category 3. (see controls in FIG. 8). Capillaries with flow velocities in group 0 (=no flow) and group 4 (=brisk flow) indicate severe circulatory failure and a severe prognosis. Preferably the methods and assessments of the invention comprise an assessment of the proportion of microvessels sampled which fall into each flow category.

In neonates circulatory failure is indicated when there is less than 20% in category 2 and less than 70% in category 3, with lower percentages, larger flow variation between capillaries and the presence of capillaries with category 0 and category 4 velocities indicating more severe failure.

CFV or mean flow-categorical velocity (MFCV) is preferably provided as a mean value, e.g. based on analysis of flow patterns in up to 40-60 microvessels, more preferably from 3-5, or possibly 3-8 video recordings over a plurality of different locations. Thus according to the methods of the invention several video sequences are obtained and the CFV or MFCV of each determined before a mean is calculated.

Heterogeneity of the CFV or MFCV is assessed using the same approach as for heterogeneity of the FCD.

Analysis of the images may be automated, whereby each image is scanned to identify the above-mentioned characteristics, e.g. using conventional recognition techniques. The values/numbers of the respective characteristics per unit area may then be calculated. In the case of CAVM, such processing may be carried out by the same computer to which the images were uploaded, or they may be transmitted to a computer for processing.

Preferably all of parameters (a) to (d) are assessed using the same instrument. While OPS or SDF may be suitable in some embodiments, particularly when it is desired to assess the microcirculation of the skin, a white light microscope, preferably CAVM is preferred.

Diffuse reflectance spectroscopy (DRS) is employed to provide a measure of oxygen saturation of erythrocytes in the microcirculation. Saturation values similar to healthy control subjects indicate no circulatory failure and/or a good prognosis. The oxygen saturation of microvascular erythrocytes ($SmvO_2$) is measured and preferably a mean value obtained. The technique is described in Awan, supra.

In preferred embodiments, oxygen extraction by the microvessels is also determined; this is calculated as follows:

$$\text{arterial oxygen saturation } (SaO_2) - SmvO_2$$

Arterial oxygen saturation is suitably measured using pulse oximetry.

A % oxygen saturation ($SmvO_2$) of less than 70% in the skin of a subject is indicative of circulatory failure or a poor prognosis; $SmvO_2$ which is less than 75% suggests there may be circulatory failure and would warrant further monitoring and increased intervention. A mean $SmvO_2$ value based on 4 to 20, more usually 5-10 or 7-10 readings, may be obtained.

The methods of the invention also comprise an assessment of the heterogeneity of $SmvO_2$ and, where appropriate, heterogeneity of oxygen extraction. The heterogeneity of $SmvO_2$ is preferably found by determining the coefficient of variance of $SmvO_2$ over a plurality of different locations, i.e. spatial heterogeneity. Patients with a CoV above 20% are likely to have circulatory, with healthy values lying within the range of 9-18%, based on around 10 repeated DRS assessments in the same skin area. Since each of the measuring volumes have a volume of fractions of 1 $mm^3$, placing the probe on the skin, removing the probe and placing the probe on the skin again for a second assessment in the same area, is sufficient to obtain data from different measuring volumes.

The output of the above analysis may comprise a separate measure for each of the characteristics (a) to (f) that were determined. These may be displayed on a monitor associated with the computer, sent to a printer, etc. Alternatively, the outputs may be combined to provide one or more scores indicative of the pathology of the microcirculation. For example, a weighted sum or average of the individual characteristics may be determined and displayed as mentioned above. An algorithm may be used to give a single output value based on a weighting applied to each parameter which may vary depending on clinical setting and patient characteristics.

The invention may also comprise the use of Laser Doppler perfusion measurements, in addition to the other measurements discussed above, in particular if the subject is a neonate. Laser Doppler (LD), quantifies perfusion in terms of flux of blood cells (mainly erythrocytes, red blood cells): Flux=number of blood cells×mean velocity in a small measuring volume (in the range of 1 $mm^3$); Lower values of Laser Doppler (LD) flux in the skin may or may not correspond to poor prognosis and may be indicative of circulatory and/or respiratory failure in adults. It was surprisingly found that when assessing neonates using LD techniques, more reliable diagnostic and prognostic information could be obtained than in adults. Without wishing to be bound by theory, it is postulated that this is due to the thinner epithelium of neonates and the incomplete differentiation of the vascular architecture into distinct layers, such that the LD signal may correlate better to the nutritive capacity of the perfusion than in adult skin.

Viewed from a still further aspect, the invention provides a method of providing clinically relevant information about a subject with or suspected of having circulatory failure comprising assessing the subject's microcirculation in respect of the following parameters:
(a) functional capillary density (FCD);
(b) heterogeneity of the FCD;
(c) capillary flow velocity;
(d) heterogeneity of capillary flow velocity;
(e) oxygen saturation of microvascular erythrocytes ($SmvO_2$); and (f) heterogeneity of $SmvO_2$;
wherein parameters (a) to (d) are assessed visually by microscopy and parameters (e) and (f) are assessed by diffuse reflectance spectroscopy (DRS).

All assessments by microscopy and DRS may be performed in real time, i.e. with the patient present, alternatively, and in some cases preferably, the methods of the invention are performed on data obtained from the patient and the patient is not still undergoing monitoring or required to be present for the analysis to take place. This applies to all the methods of the invention.

The invention extends to obtaining information that may be useful when monitoring the effect of supportive treatment for the subject. For example, it may be used in order to assess the effects on oxygen delivery to cells of a therapeutic intervention in a specific patient. The supportive treatment may comprise treatment with vasoactive or inotropic drugs, blood products and volume substitution, and even extra-corporeal life support treatment (ECLS), e.g. extra-corporeal membrane oxygenation (ECMO). In neonates, surfactants and bronchodilators may be administered and oxygen replacement therapy performed.

Thus, the present invention also provides a method of assessing the effectiveness of a therapeutic intervention on a subject with or suspected of having circulatory failure comprising assessing the subject's microcirculation visually by microscopy and by diffuse reflectance spectroscopy (DRS) to determine the oxygen saturation of erythrocytes within the micro-vessels, as described above. Typically the assessment will require an assessment before and after (optionally also during) intervention and comparison of the results obtained with one another and/or with reference values. The effectiveness of the intervention will generally be positively correlated with its ability to result in, or tend towards, a normal microcirculation. By repeated assessments according to the invention, e.g. before and after initiation of therapy directed at improving circulatory or respiratory failure, the effect of the specific therapy on the patient can be evaluated.

Today the scientific basis for selection of therapy is based on understanding of the disease mechanism (pathogenesis) as well as results from Evidence based studies. To prove statistically that Therapy A is more effective than Therapy B in a double blind, randomized and placebo controlled study in a cohort of patients, only a minority of patients treated with Therapy A may have a better outcome as compared to patients treated with Therapy B. But Therapy A may be of no value to a majority of the patients in the cohort, or even be harmful to some patients. The present invention may be used to identify which patients show improved oxygen delivery to the cells of the body after start of the therapy (by trend analysis of repeated measurements before and after start of the therapy). Likewise, it will be possible to identify patients where Therapy A is harmful and where Therapy B is beneficial. The present invention provides for the design of an optimal individualised treatment. As a result of this assessment of effectiveness of treatment, i.e. progress made by the patient, the clinician may then decide to continue, cease or alter the intervention (e.g. ECMO).

All the methods of the invention may advantageously be repeated one or more hours or one or more days apart over several hours, days or weeks. For example an individual subject may be assessed more than 3, 5, 10 or 20 times and trend analysis performed to refine the diagnosis, prognosis or, in particular, assess the effectiveness of treatment.

The methods of the invention described herein; the methods of identifying or monitoring circulatory failure, the methods of making a prognosis and of providing clinically relevant information, comprise assessment steps wherein a microscope and spectrometer are used to analyse the microcirculation of the subject, for example by applying light and a probe to the skin of the subject. As a result of these assessments, optionally utilising a comparison with reference values, information regarding circulatory failure and likely clinical outcome is obtained. Such information may give or may contribute to a diagnosis or prognosis for the subject. As a consequence, a therapeutic step may be taken, in particular to cease, continue or alter a therapeutic intervention or regimen, for example life support treatment such as ECMO. Obtaining information, making a diagnosis or prognosis and a consequential therapeutic step are steps which make up further embodiments of the methods of the invention.

Thus, for example, in a further aspect, the present invention provides a method of identifying or monitoring circulatory failure in a subject, which method comprises assessing the subject's microcirculation in respect of the following parameters:
  (a) functional capillary density (FCD);
  (b) heterogeneity of the FCD;
  (c) capillary flow velocity;
  (d) heterogeneity of capillary flow velocity;
  (e) oxygen saturation of microvascular erythrocytes ($SmvO_2$); and (f) heterogeneity of $SmvO_2$;
    wherein parameters (a) to (d) are assessed visually by microscopy and parameters (e) and (f) are assessed by diffuse reflectance spectroscopy (DRS); and wherein subsequent to said assessment a therapeutic step is taken, in particular to cease, continue or alter a therapeutic intervention or regimen which the subject is receiving.

The patient may be a non-human animal or a human, but is preferably a human.

The present inventor has surprisingly shown that microscopy and DRS together can be used to generate meaningful data regarding the health of neonates through analysis of their microcirculation. It was not expected that neonates, whose skin is not fully developed, would show such similarities in their microcirculation to adults and that reproducible and reliable information about newborn microvasculature/microcirculation could be obtained using non-invasive techniques compatible with caring for vulnerable and possibly very sick babies. Such information permits diagnostic and prognostic conclusions, in particular regarding circulatory or respiratory failure.

The inventor has recognised that the state of a neonate's microcirculation provides valuable insight when seeking to optimize therapy for sick and/or premature neonates. When signs of circulation failure are clinically recognized now, the failure has already become severe. When the circulation starts to be insufficient, the body has regulatory mechanism which give priority to some tissues and cells over others, for example the brain and the heart (coronary) circulation has priority over skin cell and thermoregulatory skin perfusion. The present invention can look at the quality of perfusion to the cells in the skin. With increasing failure more cells will be affected and lead to organ failure, until insufficient oxygen delivery to vital organs like the brain and the heart leads to death. In this continuum of circulatory failure, from affecting some skin cells to affecting vital organs resulting in death, a key question is at what degree of severity does the responsible physician recognize the failure problem. It is believed that the identification/diagnosis of circulatory failure with the present invention can be made at an earlier stage than is the case today and that this increase in sensitivity and the earlier recognition of circulatory failure, will result in earlier therapeutic interventions and to better clinical outcome than is achieved today.

Accordingly, in a further aspect, the present invention provides a method of identifying circulatory or respiratory failure in a neonate, which method comprises assessing the neonate's microcirculation visually by microscopy and by diffuse reflectance spectroscopy (DRS) to determine the oxygen saturation of erythrocytes within the microvessels.

"Respiratory failure" does not imply a total failure but an insufficient uptake of oxygen.

Any condition which causes respiratory or circulatory failure may result in retarded development, sickness, permanent organ dysfunction or even death of a neonate. Many conditions and complications which can lead to respiratory or circulatory failure are associated with the transition from intra- to extrauterine life, in particular the changes that occur in the transition from fetal to neonatal circulation, these may all be exacerbated in premature babies. Conditions which can cause respiratory or circulatory failure include respiratory distress syndrome (RDS), persistent pulmonary hypertension (PPHN), anaemia, hypo-volemia, infectious conditions (sepsis) as well as congenital malformations in the respiratory or circulatory systems.

The invention is particularly applicable to premature neonates, i.e. born after less than 37 weeks of pregnancy (from the first day of the last menstrual period), more particularly to neonates born after less than 32 weeks of pregnancy.

Particularly in these patient groups, it may be desirably to perform the assessment method described herein even when there are no symptoms suggesting circulatory or respiratory failure. In such circumstances, the scores obtained by the present assessments can give an early warning of circulatory and/or respiratory failure as the quality of the microcirculation reveals itself to be below healthy levels. Thus, such early indications also constitute 'circulatory or respiratory failure' as defined herein.

The invention also extends to an apparatus for carrying out the methods discussed herein. Thus, viewed from a further aspect there is provided apparatus for assessing a subject's microcirculation comprising a microscope, a spectrometer and a computer, whereby the computer is arranged to receive image(s) of the microcirculation obtained using the microscope and data relating to $SmvO_2$ from the spectrometer and, optionally, to process the image(s) and data to identify and/or determine characteristics/parameters associated with pathology, wherein the image(s) and data relate to the following parameters:
 (a) functional capillary density (FCD);
 (b) heterogeneity of the FCD;
 (c) capillary flow velocity;
 (d) heterogeneity of capillary flow velocity;
 (e) oxygen saturation of microvascular erythrocytes ($SmvO_2$); and
 (f) heterogeneity of $SmvO_2$.

Software for analysis of the collected frames/films and the spectrometer curves can be installed on the same computer, but analysis may also be performed on a separate computer after the collected files has been transferred to this other computer. The first computer (receiving computer) can have installed software for real time analysis, both for DRS and for CAVM files. Preferably, offline analysis is performed on another computer (processing computer), just as in a professional biochemical lab that receives blood samples from a (general practitioner) GP.

Typically analysis of the images and data will involve some computer processing and some analysis by individuals who are experienced in interpretation of the images/data.

The microscope is preferably used to obtain the image(s) from the skin or other part of a patient's body, and is then removed therefrom prior to the processing steps. Likewise, a probe attached to the spectrometer is preferably used on the body and then removed prior to the processing steps. Indeed, a further aspect of the invention relates to the apparatus for processing previously acquired data.

Thus, viewed from a still further aspect there is provided apparatus for assessing a subject's microcirculation comprising a computer arranged to receive image(s) of the microcirculation of a neonate obtained using a microscope and data relating to $SmvO_2$ from a spectrometer and to process the image(s) and data to identify and/or determine characteristics/parameters associated with pathology, wherein the image(s) and data relate to the following parameters:
 (a) functional capillary density (FCD);
 (b) heterogeneity of the FCD;
 (c) capillary flow velocity;
 (d) heterogeneity of capillary flow velocity;
 (e) oxygen saturation of microvascular erythrocytes ($SmvO_2$); and
 (f) heterogeneity of $SmvO_2$.

The apparatus preferably further comprises a means for outputting values corresponding to the characteristics/parameters and/or a value based on them in combination, such as a weighted sum or average. Such a value may be regarded as a microvascular pathology score. An algorithm can be used to process the raw data such that each of the parameters defined herein is given a weight, weights may be optimised for different patient cohorts, e.g. for premature or for full term neonates. The output value of the algorithm typically corresponding to a weighted sum or average.

The invention also extends to software, whether in tangible form on a data carrier, or downloadable via a network, comprising instructions to cause a computer to carry out the processing and/or output steps mentioned above.

The invention further extends to the use of such an apparatus and/or such software to assess the subject's microcirculation and to identify circulatory failure, to provide a prognosis and/or to monitor the efficiency of a treatment regimen or intervention based on that measurement/those measurements.

In a further aspect the present invention provides a computer implemented method of identifying or monitoring circulatory failure in a subject, which method comprises assessing the subject's microcirculation in respect of the following parameters:
 (a) functional capillary density (FCD);
 (b) heterogeneity of the FCD;
 (c) capillary flow velocity (FCV);
 (d) heterogeneity of FCV;
 (e) oxygen saturation of microvascular erythrocytes ($SmvO_2$); and
 (f) heterogeneity of $SmvO_2$;
 wherein parameters (a) to (d) are assessed visually by microscopy and parameters (e) and (f) are assessed by diffuse reflectance spectroscopy (DRS).

An embodiment of the invention will now be described, by way of example only, with reference to the accompanying drawings:—

Figure 3:
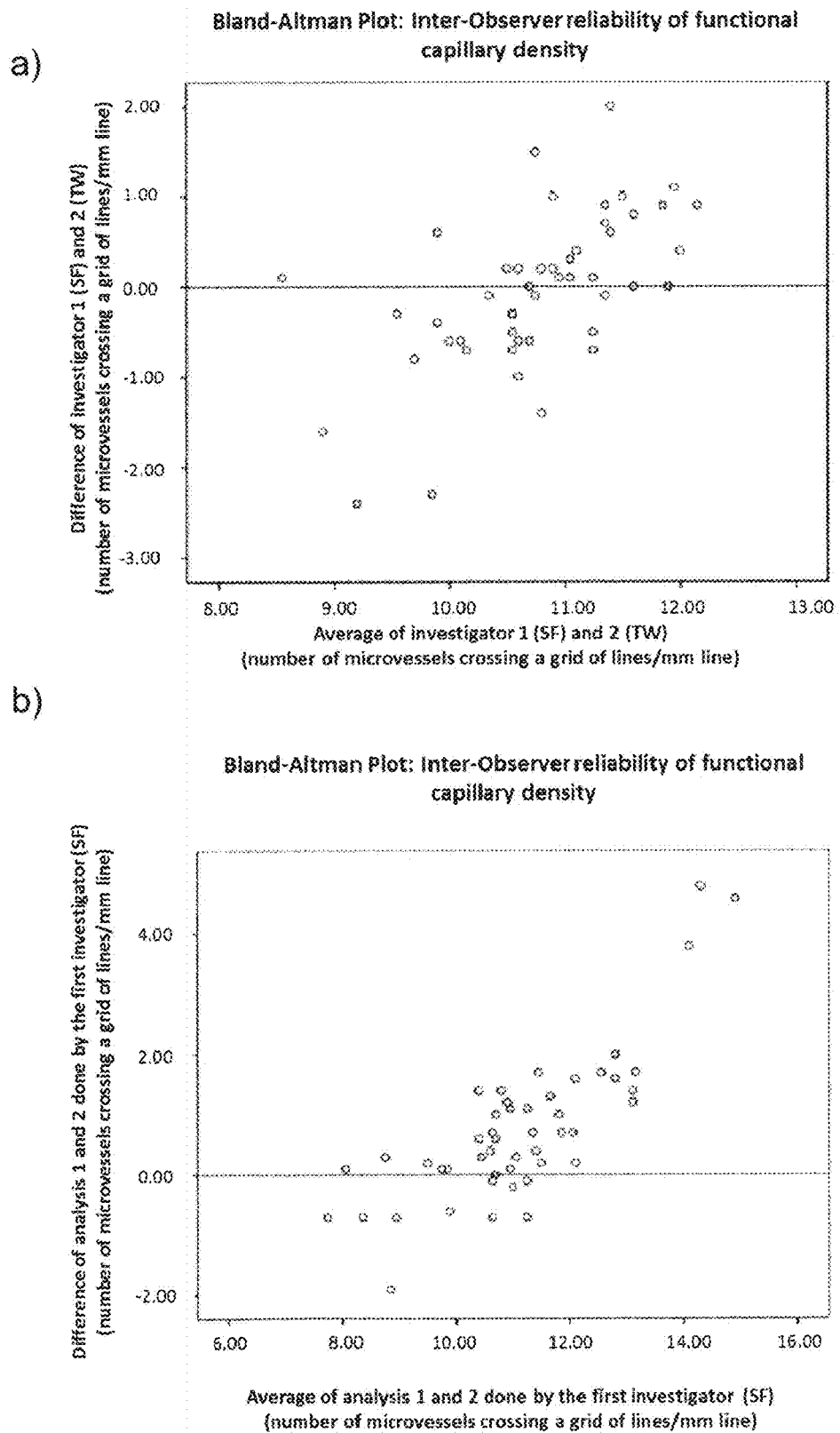
Figure 4:
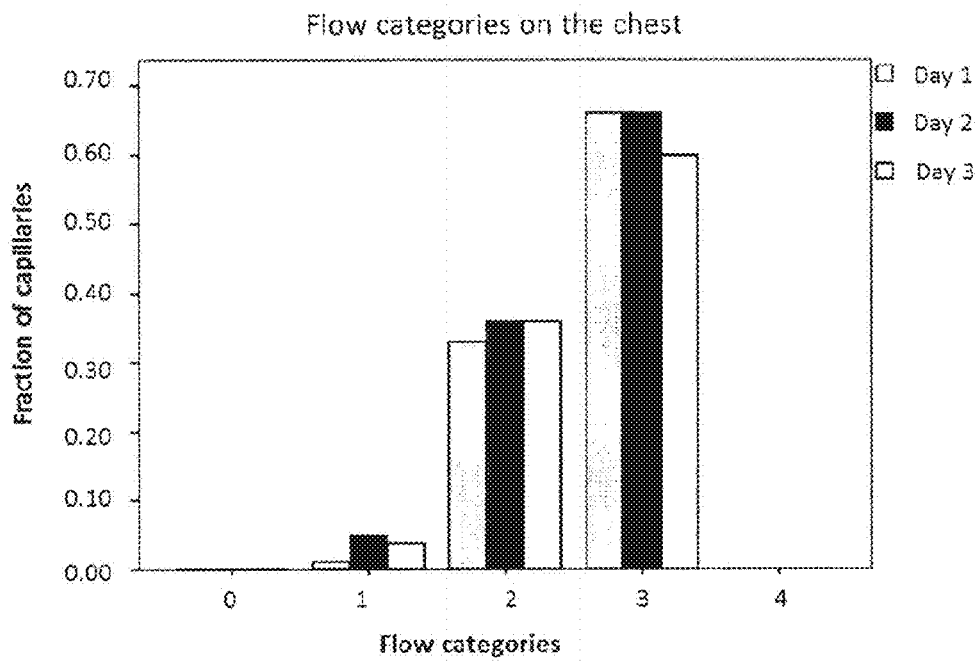
Figure 4:
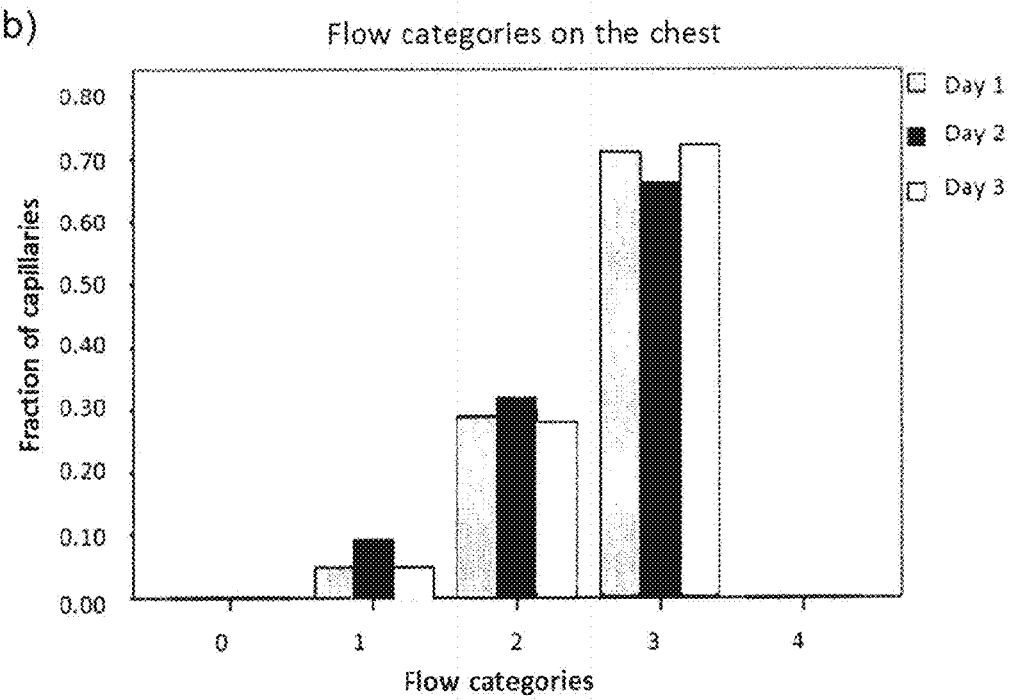

FIGS. 3 (*a*) and (*b*) are Bland-Altman plots showing inter-observer (a) and intra-observer (b) reliability of functional capillary density measurements;

FIGS. 4 (*a*) and (*b*) are graphs showing capillary flow categories in the chest (a) and head (b).

Figure 1:
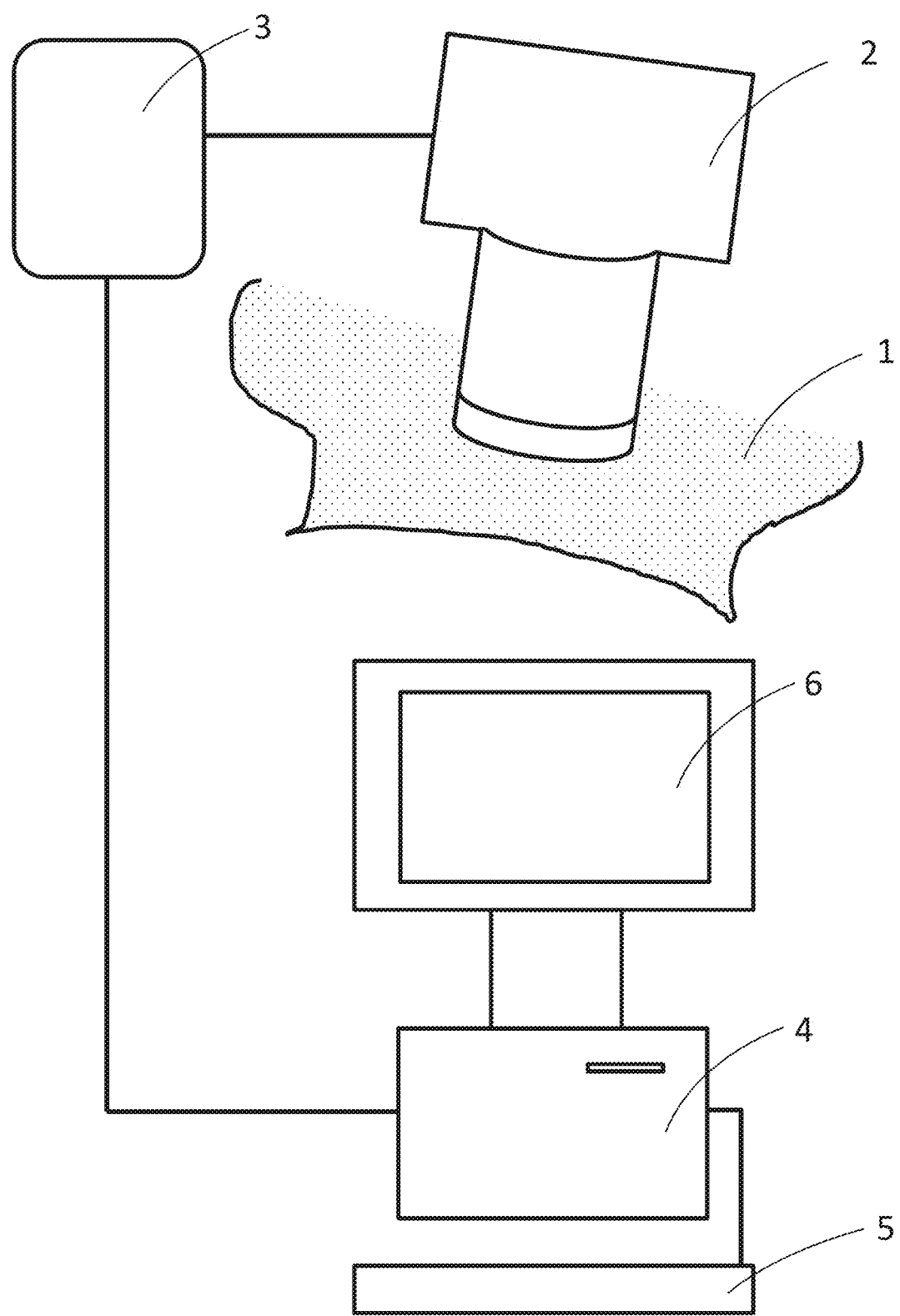
FIG. 1 is a schematic illustration of an apparatus for assessing a neonate's microcirculation by microscopy.

With reference to FIG. 1, there is shown a part of a patient's body 1, a hand-held video microscope head 2, video microscope controller 3, computer 4, keyboard 5 and display unit 6.

The microscope head 2 is shown in contact with the patient's body 1 as it would be when acquiring images therefrom under the control of microscope controller 3. Once images have been obtained, the microscope head 2 is removed from the patient's body 1.

Images are passed via the microscope controller 3 to the computer 4 for processing. This involves analysis of the images to identify and measure/quantify the following:—
 (a) optionally pericapillary bleedings and/or dark haloes (number per unit area);
 (b) functional capillary density (FCD) (number per unit area);
 (c) heterogeneity of the FCD (coefficient of variation);
 (d) CFV or MFCV;
 (e) heterogeneity of CFV.

In one variant of the embodiment, these characteristics are displayed on a screen for identification/analysis by a human operator who then makes appropriate entries of representative values via the keyboard 5. In another variant, image recognition software identifies capillaries (and associated bleedings and haloes) and speed of blood flow therein and assigns values automatically The computer then calculates a weighted sum of these values and outputs this to the display 6, along with the values on which it is based. This score, together with scores for SmvO$_2$ is indicative of the degree of pathology of the neonate's microcirculation.

Figure 2:
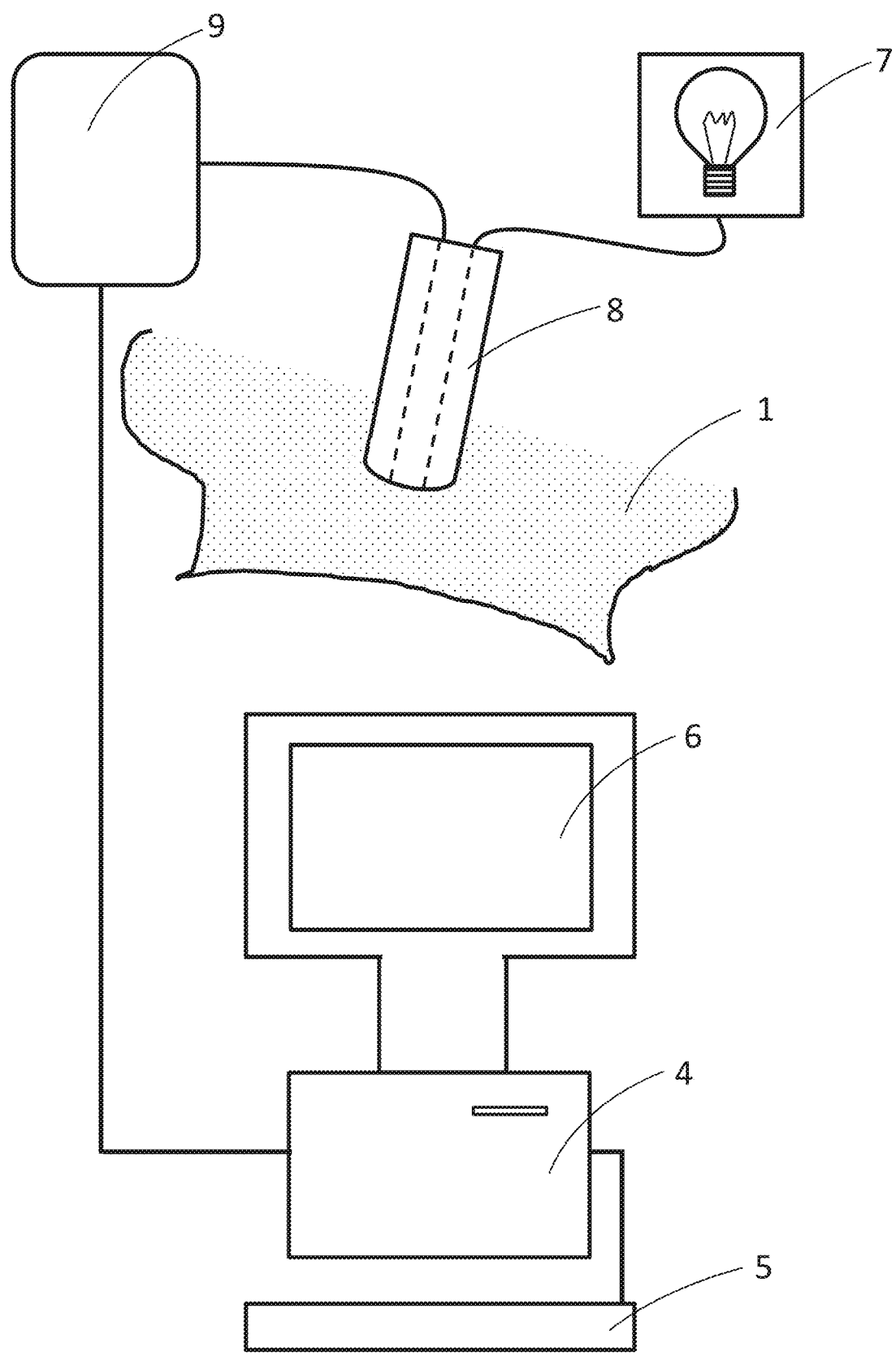
FIG. 2 is a schematic illustration of an apparatus for assessing a neonate's microcirculation by DRS.

With reference to FIG. 2, there is shown a part of a patient's body 1, a light source 7, a probe 8, a spectrometer 9, computer 4, keyboard 5 and display unit 6.

The probe 8 is shown in contact with the patient's body 1 as it would be when it is emitting light received by an optical fibre from the light source 7 and receiving reflected light from the body, this reflected light being transmitted via an optical fibre to the spectrometer 9. Once the reflected light has been processed by the spectrometer 9, the probe 8 is removed from the patient's body 1.

Data from the spectrometer 9 are passed to the computer 4 for recordal and processing. The spectrometer 9 generates data in the form of reflectance spectra, decomposition of the spectra is performed by the computer 4 to estimate SmvO$_2$ and the heterogeneity of SmvO$_2$. The computer then calculates a weighted sum of these values and outputs this to the display 6, together with the values on which it is based. This score, together with the score based on visual analysis is indicative of the degree of pathology of the neonate's microcirculation.

In one embodiment the spectrometer 9 and microscope controller 3 are connected to the same computer 4. The computer 4 may analyse the collected frames/films and the spectra. In another embodiment, the frames/films and spectra may be transferred to another computer for analysis and computer(s) 4 act only to receive the data from the microscope controller 3 and spectrometer 9.

A clinical study based on a further embodiment, which further comprises the use of laser Doppler perfusion measurements of neonates has been carried out and is discussed in Example 2.

The present inventor was the first to appreciate the prognostic utility of analysis of the microcirculation of ICU patients. Thus, in a further aspect, the present invention provides a method of making a prognosis for a patient with circulation failure being considered for, or undergoing, intensive care therapy, comprising assessing the state of the patient's microcirculation.

This aspect of the invention is particularly applicable to patients with systemic circulation failure, for example following acute cardiac pump failure, hypovolemia or sepsis, and the supportive treatment may comprise extra-corporeal life support treatment (ECLS), e.g. extra-corporeal membrane oxygenation (ECMO). The invention extends to monitoring the effect of the supportive treatment for said patient by the same means.

Examinations according to the invention can be used to make a prognosis and hence improve selection of patients for life supporting treatments such as ECMO/ECLS and/or to guide such therapy as well as providing an indication of the effect of additional supportive therapy and the benefit in continuing with treatment i.e. to provide stop criteria for life supporting treatment.

An embodiment of this aspect invention will now be described, by way of example only, with reference to the accompanying further drawings:—

Figure 5:
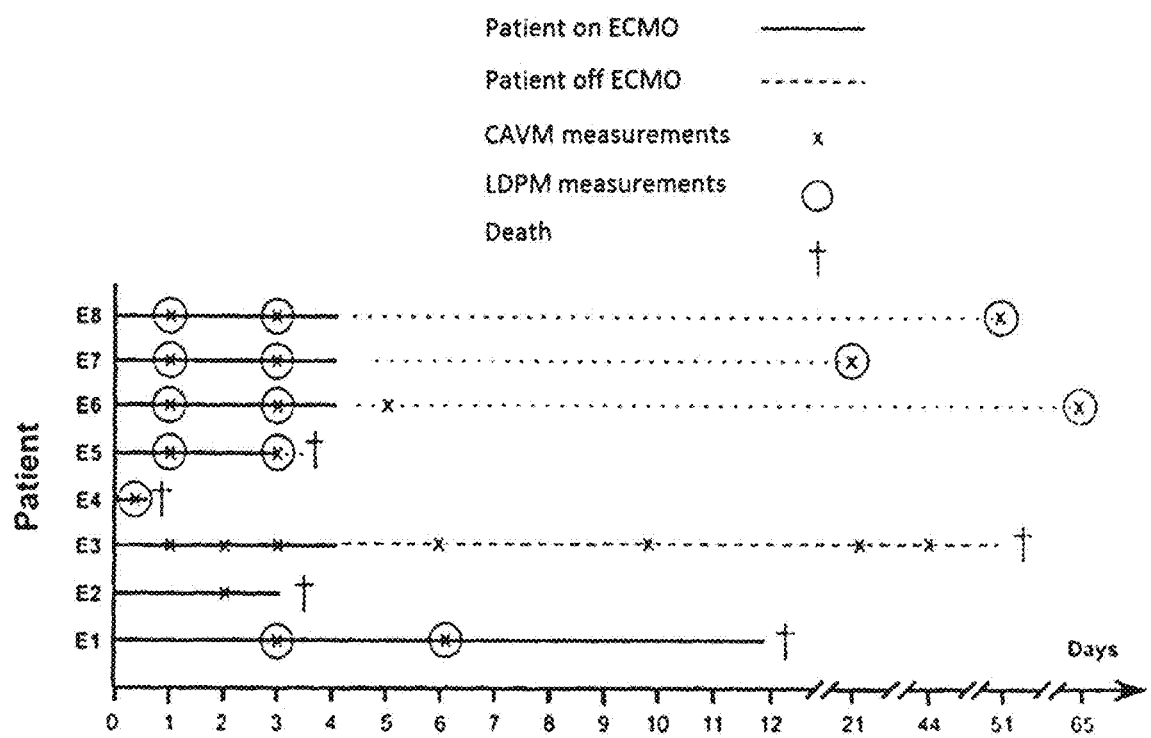
Figure 6:
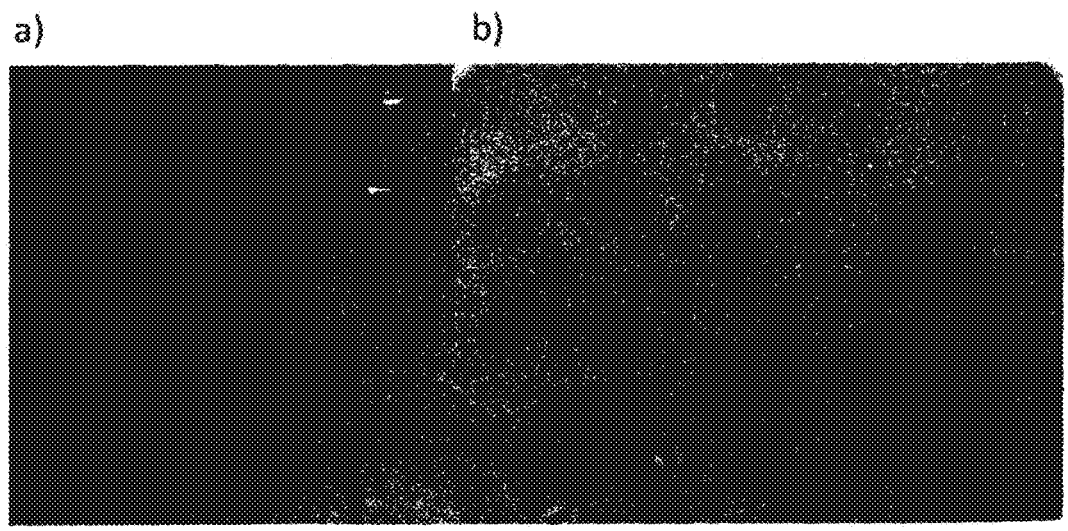
Figure 7:
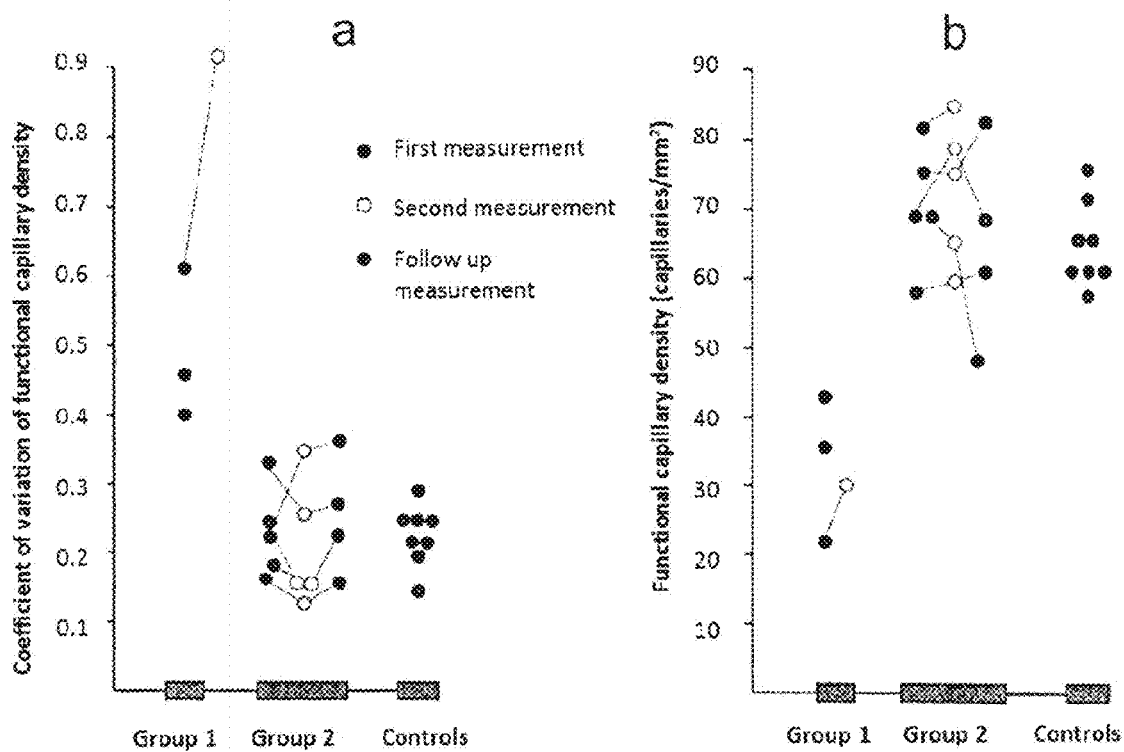
Figure 8:
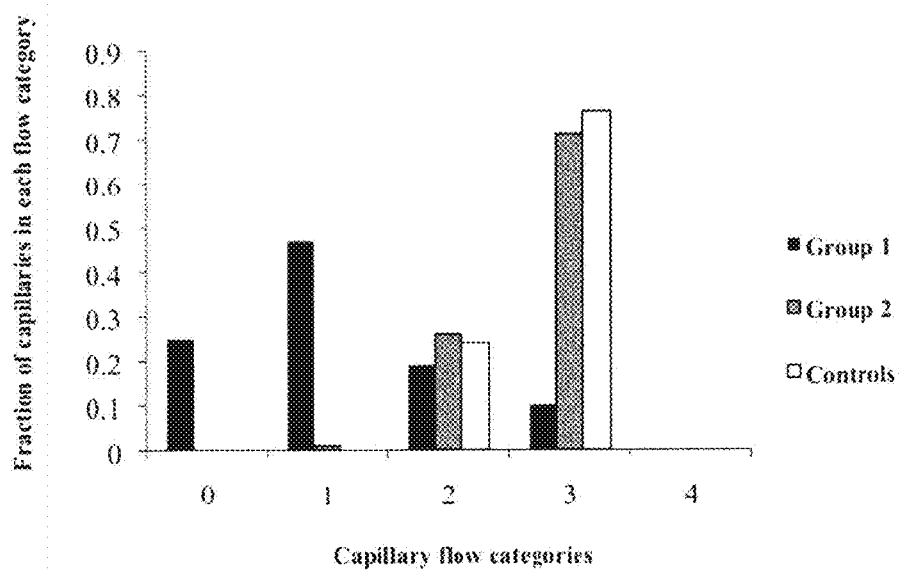

FIG. 5 is an overview of eight ECMO patients;

FIGS. 6 (a) and (b) are microscope images showing pen-capillary bleedings and dark haloes respectively;

FIGS. 7 (a) and (b) are graphs showing functional capillary density for three groups of ECMO patients and healthy controls; and FIG. 8 is a histogram showing the proportions of capillaries in various blood flow categories for three groups of ECMO patients.

With reference to FIG. 1, there is shown a part of a patient's body 1, a hand-held video microscope head 2, video microscope controller 3, computer 4, keyboard 5 and display unit 6.

The microscope head 2 is shown in contact with the patient's body 1 as it would be when acquiring images therefrom under the control of microscope controller 3. Once images have been obtained, the microscope head 2 is removed from the patient's body 1.

Images are passed via the microscope controller 3 to the computer 4 for processing. This involves analysis of the images to identify and measure/quantify the following:—
 (a) pericapillary bleedings and/or dark haloes (number per unit area);
 (b) functional capillary density (FCD) (number per unit area);
 (c) heterogeneity of the FCD (coefficient of variation);
 (d) capillary flow-categorical velocity profiles
 (e) mean flow-categorical velocity (i.e. speed of flow in capillaries).

In one variant of the embodiment, these characteristics are displayed on a screen for identification/analysis by a human operator who then makes appropriate entries of representative values via the keyboard 5. In another variant, image recognition software identifies capillaries (and associated bleedings and haloes) and speed of blood flow therein and assigns values automatically.

The computer then calculates a weighted sum of these values and outputs this to the display 6, along with the values on which it is based. This score is indicative of the degree of pathology of the microcirculation.

Figure 9A:
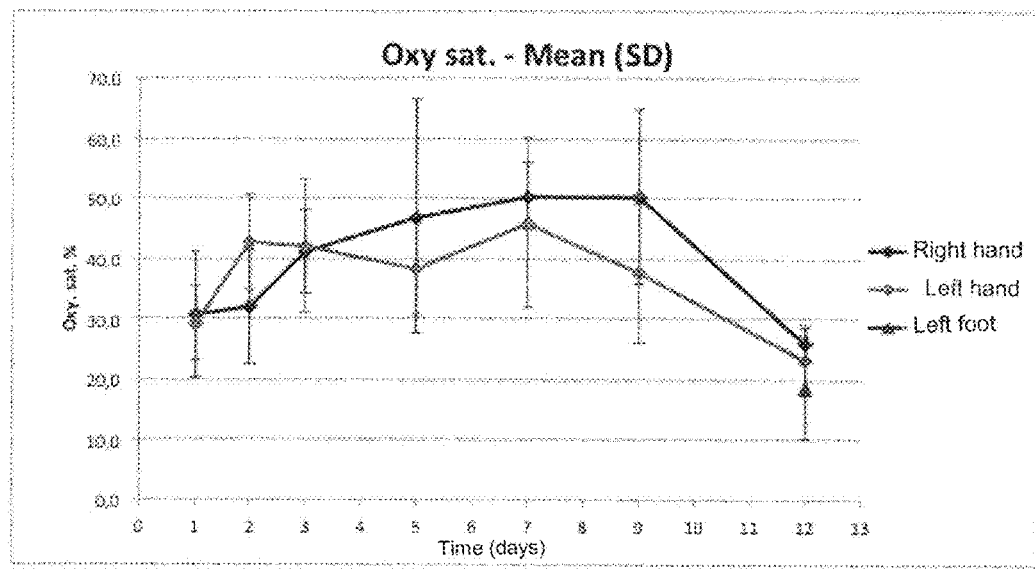
Figure 9B:
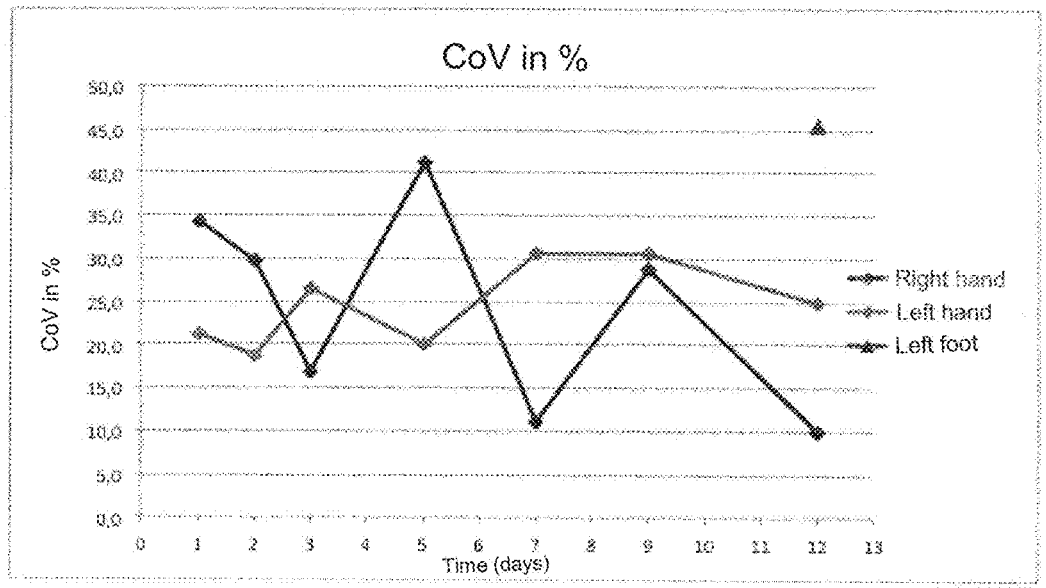

The invention is further illustrated in the following Examples in which:

FIGS. 9(a) and (b) are graphs showing (a) oxygen saturation as a mean % value over time as measured by DRS and described in Example 5; and (b) the CoV of the values for oxygen saturation presented in (a).

Figure 10:
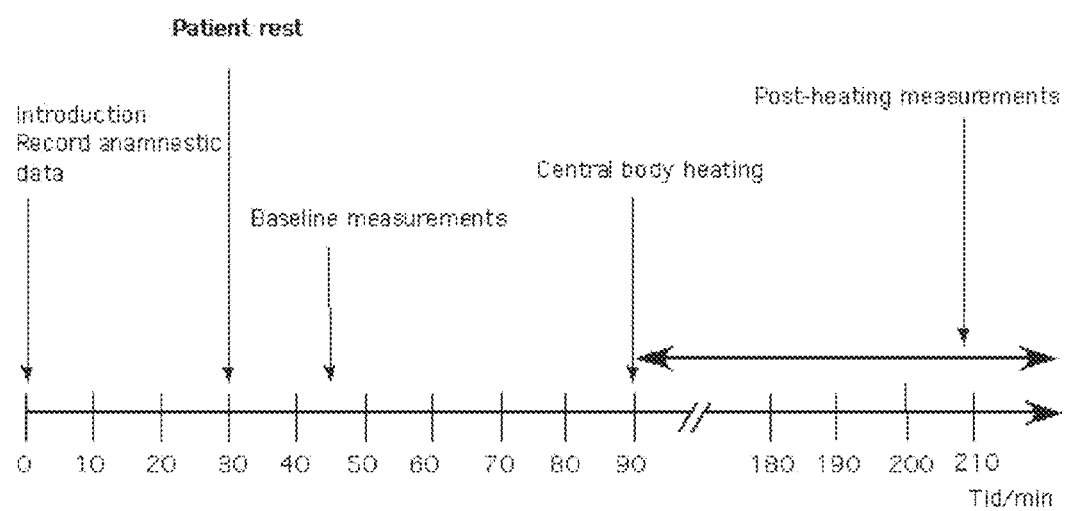

FIG. 10 is flow chart showing the timeline for the patient protocol being applied.

EXAMPLE 1

1 Patients and Methods
1.1 Patients

Over a period of two years, patients treated with ECMO for cardiogenic shock in a medium sized cardiac surgical unit (approximately 550 open heart operations per year) were candidates for inclusion. Eight consecutive patients (E1-E8), two females and six males; median age 59 years (range 27-78), were included. No patients were excluded from the study. Four patients (E4-E7) were in a state of cardiogenic shock before reaching the operating theatre: one secondary to massive pulmonary embolism with ongoing mechanical cardiac compression (E4), one with massive myocardial infarction (MI) (E5), one with acute MI and complication to percutaneous coronary intervention (PCI) (E6) and finally one with endocarditis (E7). The remaining four patients suffered from post cardiotomy cardiogenic shock. Eight healthy, non-smoking male students (21-29 years old) served as controls.

1.2 Extra-Corporeal Membrane Oxygenation (ECMO)

Arterial cannulation was performed in the groin in seven patients, in two of them via an end to side Dacron graft. One patient had arterial cannulation via the right subclavian artery. Seven patients had vein drainage via the femoral vein and one via the right atrium. The ECMO-circuit consisted of a centrifugal pump (Medtronics Incorporated, Minneapolis, Minn., USA), a heparin coated membrane oxygenator and tubes (Maquet Cardiovascular 72145 Hirrlingen, Germany). After establishing ECMO, all patients were initially treated with a flow of at least 4.0 l/min. Maintenance therapy on ECMO was guided by a standard protocol for the unit [38]. Weaning from ECMO was guided by trans-oesophageal ECCO Doppler in addition to clinical parameters.

1.3 Microvascular Techniques

Skin microcirculation was evaluated with video microscopic measurements in eight patients and Laser Doppler measurements in six.

1.3.1. Computer Assisted Video Microscopy (CAVM)

This technique involves a hand-held video-microscope applied gently on the surface of the region of interest (ROI). Immersion oil is used. Pictures or film sequences are projected and stored on a computer. For the first patient, E1, a less advanced microscope, with a 1.3 megapixel CCD, (ProScan, Bodelin technologies, OR, USA), magnifying 200 times was used. With this microscope pericapillary pathology, functional capillary density (FCD) and heterogeneity could be evaluated, but not capillary flow patterns. The remaining patients (E2-E8) were examined with another microscope (Microvision 2100, Finlay Microvision Co. Ltd., Warwickshire, UK) with higher resolution and a 500 times magnifying lens. An analogue to digital converter (Canopus, Kobe, Japan) was used to project and store the film sequences on a Mac Book pro, using the software iMovie (both Apple, Cupertino, USA).

To study pericapillary pathology, calculate functional capillary density (FCD), heterogeneity of FCD and microvascular flow patterns in a ROI, the first five captured film sequences with adequate quality were used. A grid with four equally sized rectangles was made to facilitate visual analysis. The software Xscope (the Iconfactory, Greensboro, N.C., USA) was used for creating the grids.

Adequate film quality was defined as focused capillaries in all four quadrants of the frame and sequence duration of at least ten seconds. FCD was defined as the mean number of visible capillaries per square millimetre. Heterogeneity of FCD was expressed as the coefficient of variation (CoV=SD/mean) of the density of capillaries in each of the four rectangles in the five film sequences (n=20). For analysis of flow velocity, each capillary of the five film sequences were visually scored into one of five groups from "no flow" (Category 0) to "brisk flow" (Category 4), and expressed in fractions (Fr=number of capillaries in each category/total number of capillaries). Based on the fractions of capillaries in each flow category, mean flow-categorial velocity was calculated in the following way:

Mean flow-categorical velocity=$\{Fr(1)\times 1\}+\{Fr(2)\times 2\}+\{Fr(3)\times 3\}+\{Fr(4)\times 4\}$.

1.3.2 Laser Doppler Perfusion Measurements (LDPM)

LDPM is a technique for quantification of microvascular perfusion. The output of the technique is given in a semi-quantitative scale of flux, defined as the product of number of moving blood cells and their mean velocity in the measured volume ($<1$ mm$^3$).

A Moor Blood Flow Monitor (MBF 3D) for perfusion measurements with Moorsoft (both Moor instruments, Axminster, Devon, England) was used for recording and analysis. Flux in a ROI was given as the mean value of seven consecutive measurements of a ten-second duration.

1.2.4. Measuring Procedure

FIG. 6 shows skin microcirculation in fossa tabatiere in two ECMO patients. To the left (a) several pericapillary bleedings are seen, and hardly no dot-liked capillaries are present (Patient E1, ProScan ($\times$200)). To the right (b) circular dark haloes are surrounding capillaries with no flow or extremely slow sluggish flow are seen (Patient E2 Microvision 2100 ($\times$500)).

The first microvascular examinations were performed as soon as possible, usually within 24 hours after establishing ECMO. The second measurement was performed on day 3 when possible. E4 was examined twice with an interval of only two hours before the ECMO was turned off due to ceased cerebral blood flow. Four survivors (Group 2) were controlled 18-65 days after weaning off ECMO. E3 was examined seven times. The skin on the dorsum of the hand, between the first and second metacarpus (fossa tabatiere) was examined by CAVM in all patients. From patient 3 and onwards we also assessed the skin perfusion of the medial side of the right foot, with the ROI being located one third of the distance on an imaginary line from the medial malleolus to the caput of the first metatarsus. In the patient with pericapillary bleedings (E1), additional skin areas, such as over arm, thigh, chest, and face were also examined. Six patients were measured by LDPM. Patient E1 was only measured in fossa tabatiere. From patient 4 and onwards LDPM was measured on the foot as well. CAVM and Laser Doppler measurements were performed in both locations in all controls. At the time of microvascular measurements, the corresponding central hemodynamic parameters, results from blood tests and clinical parameters were noted.

1.5 Ethical Considerations

The decision to establish ECMO was taken by the responsible surgeon solely on clinical grounds. All microvascular measurements were non-invasive, and performed only after approval from the responsible surgeon and anesthesiologist. No results of microvascular findings influenced maintenance therapy on ECMO. Since patients on ECMO could not give an informed consent, next of kin, when available, consented to the microvascular assessments. Long-term survivors (n=3) gave their consent to follow-up measurements and to publication of their data. The Regional ethics committee has approved publication of data from all eight patients.

1.6 Statistics Data are presented as means with range. The coefficient of variation (CoV) was used as a parameter for heterogeneity of functional capillary density. For comparing results between outcome groups, independent t-test was used.

2 Results 2.1 Clinical Information and Outcome

An overview of clinical information of the individual patients, laboratory data, and performed examinations is given in tables 1, 2 (see Annex at end of this Example) and FIG. 5. FIG. 5 is an overview over the eight ECMO patients, from start of the ECMO treatment till death or last control measurement. Measurement periods are marked according to measuring technique.

The patients were grouped according to clinical outcome into two groups: patients dying on ECMO (Group 1) and patients surviving ECMO (Group 2). Mean age for group 1 was 44 years, for group 2 it was 58 years. Both sexes were present in each group. In group 2, one patient had a recovery of heart function and a maintained cerebral function but died from bleeding complications in the intensive care unit. Of the remaining four patients in group 2, one patient (E3) was transferred to another hospital where he died from multi organ failure on day 51 after establishing ECMO. The remaining three were still alive and out of institutions two years after the ECMO treatment.

2.2 Clinical Measurements

White blood cell count, during the first microvascular measurements, was lower among survivors as compared with non-survivors, table 2.

2.3 Microvascular Measurements 2.3.1. Computer Assisted Video Microscopy (CAVM)

2.3.1.1 Pericapillary Pathology:

E1 had numerous pericapillary bleedings in several skin locations (fossa tabatiere, volar side of forearm, leg and face) on both examinations, FIG. 3 (a). No other patients had any visible pericapillary bleedings. Patients E2 and E4 had circular dark haloes at a distance of 12±1 microns around some skin capillaries (65% in E2 and in 14% in E4), see FIG. 3 (b).

2.3.1.2 Functional Capillary Density (FCD):

FIG. 4 shows functional capillary density (in capillaries/mm$^2$) for three groups of ECMO patients and eight healthy controls (b) and coefficient of variation of functional capillary density for the same patients (a). For patients measured more than once, the first, second and follow-up measurements are given. The follow-up measurements were performed 18-65 days after the patient was successfully weaned off ECMO (n=4).

The three patients dying on ECMO had significantly lower FCD in fossa Tabatiere compared with patients surviving ECMO (p=0.002), FIG. 4 (b). No difference in FCD was seen between patients in group 2 and the controls (p=0.24).

From patient E3 onwards, measurements were also performed on the medial side of foot (n=6). In this location the patients had an FCD of 66.2 (range 55.6-75.8) capillaries/mm$^2$, similar to mean FCD of the hand in patients surviving ECMO (70.8 capillaries/mm2) and controls (65.5 capillaries/mm2), as well as in the foot of controls (66.2 capillaries/mm2). Since only one patient in group 1 (E4) was measured on the foot, no further analysis was done on data from this location. Still, E4 had the lowest FCD and the highest CoV of FCD of the measured patients in this location.

The second measurements of FCD in fossa tabatiere gave values similar to the first measurements.

Final follow-up measurements of four (patient E5 had already died) patients in group 2 were performed 18-65 days after weaning off ECMO, FIGS. 5 and 7. One patient showed a reduced FCD on final assessment (E3, see later), while the rest of the survivors had a mean FCD of 65.5 (range 56.9-76.5) on final assessment, values in the same range as their first measurement and in controls in this location.

2.3.1.3 Heterogeneity of FCD:

Patients dying on ECMO (group 1) had significantly higher CoV of skin capillaries compared with patients in group 2 (p<0.005), FIG. 7 (a). No difference was seen between the latter group and controls (p=0.74).

2.3.1.4 Capillary Flow Patterns:

The mean flow-categorial velocity during the first measurements in fossa tabatiere showed no difference between patients surviving ECMO, 2.67 (range 2.53-2.87)), and controls with 2.76 (range 2.65-2.88) (p=0.17). The two patients that died on Zo ECMO had mean flow velocities of 0.5 and 1.76, significantly lower than the patients surviving ECMO (p=0.007). In one of these patients with pericapillary dark haloes (E2), erythrocyte movement in the capillaries was hardly detected in any of the film sequences, although the ECMO circuit gave an output of 4.5 litre/min. All capillaries in healthy controls had flow patterns 2 or 3, FIG. 8. Patients in group 2 had a similar flow category distribution as the controls. In the two patients in group 1 where capillary flow assessments were performed (E2, E4); the capillaries had a broadened and a left-shifted spectrum. Flow category 0 (no flow) and 1 (sluggish flow) was hardly seen in patients surviving ECMO and never seen in controls. E3 had a prolonged and complicated stay in the ICU with lung infections, sepsis episodes, and progressive renal failure after ECMO treatment. The patient died 51 days after ECMO was established due to multi organ failure. The patients final microscopy assessments on day 44 showed that FCD was reduced with 30%, CoV was increased with 64% and the mean flow-categorial velocity was reduced to 1.75, a reduction of 34%, compared with the initial measurements. On one occasion the patient was examined during an episode with gram negative sepsis (day 24); at that time the FCD was markedly reduced to 49 capillaries/mm2 (−29%), the CoV was 0.17 (−23%), and 22% of the skin capillaries had brisk flow (category 4). Capillaries in this flow category were not observed for any other patients at any time.

2.3.2 Laser Doppler Perfusion Measurements (LDPM)

The controls had a mean flux value of 48 Au (range 22-96) in fossa Tabatiere, while the corresponding values at the medial side of the foot were 31.5 (range 17.4-60.1). The mean coefficient of variation was 0.20 (range 0.13-0.35) in fossa Tabatiere, and 0.25 (range 0.12-0.34) at the medial side of the foot.

The laser Doppler data sets for patients are incomplete. The patients that died on ECMO (E1 and E4) had lower flux values in both locations and on both measuring occasions than any of the surviving patients or controls (tab. 3), but the differences did not reach significance, probably due to small numbers and large variability. The coefficient of variation for flux in fossa Tabatiere was significantly higher in the survivors as compare with the controls at the first measurement (p=0.03), but not for the second and third measurement at the same locations (p=0.17 and 0.74 respectively). On the medial side of the foot, coefficient of variation did not show significant changes between survivors and controls (p=0.22, 0.44 and 0.82 respectively).

3 Discussion

The study was undertaken in a medium sized unit for heart surgery, with approximately 550 open heart operations a year. Both the incidence of patients in need of ECMO (0.6%) and survival of patients treated with ECMO (28%) are comparable with data from the literature. Except for white blood cell count no clinical parameters showed significant differences between the survivors and non-survivors. Significant changes were seen for all parameters of CAVM. Skin microvascular anatomy is complex with subpapillary capillaries mainly serving nutrition for epithelial proliferation and deeper vascular plexus mainly serve body temperature regulation. In adult skin, only the sub-papillary capillaries are seen in most locations with the microscopy equipment used in this study. The Laser Doppler techniques measure both superficial and the deeper plexus perfusion.

3.1 Observations Made with Computer Assisted Video Microscopy (CAVM).

3.1.1 Functional Capillary Density and Heterogeneity of Capillary Distribution:

In 1920 the Danish physiologist August Krogh was awarded the Nobel Prize in Physiology or Medicine. One of his main achievements was the identification of the "Krogh cylinder", postulating that all cells need to be located within a critical radius of a perfused capillary to survive. Cells outside this radius would experience insufficient oxygenation independent of the flow rate and erythrocyte oxygen saturation in the nearest capillary. An uneven distribution of perfused capillaries may give low oxygen tension to some cells in spite of normal $SaO_2$.

The patients that died on ECMO had reduced FCD and increased CoV of FCD compared with patients surviving ECMO and healthy controls. The patients surviving ECMO had stable FCD and CoV within the reference levels for the controls (FIG. 7). The exception was patient E3, who had a complicated post ECMO course with several septic episodes. The last assessments, seven days before he died from multi organ failure, showed values comparable to the patients dying on ECMO see FIG. 7.

In 1922 Freedlander used a microscope to show a decreased capillary density in skin in septic patients. Later studies confirmed Freedlanders findings and demonstrated increased heterogeneity of FCD in different tissues and mammalian species with systemic diseases. In patients with septic and cardiogenic shock a persistent severely reduced FCD for 24 hours in the sublingual area, is associated with increased mortality. Reduced FCD in the rectal mucosa is associated with poor prognosis in patients with severe malaria.

3.1.2 Capillary Flow-Patterns:

FIG. 7 shows distribution of capillaries in each of five flow categories for patients dying on—(group 1), and patients successfully weaned off ECMO (group 2) as compared to eight healthy controls. Flow categories were defined as: 0=no flow; 1=sluggish flow (very slow cell movement, sometimes backward flow); 2=continuous low flow (cells moving continuously forward, mostly slowly); 3=continuous high flow (cells moving continuously forward, mostly rapid); 4=brisk flow (rapidly moving cells throughout the entire film sequence).

In the two patients in group 1, in whom capillary flow had been analysed, a significant number of capillaries with "no flow" or "sluggish flow" were seen. These categories were hardly seen in controls or survivors. Patients in group 2 had capillary flow pattern similar to the controls. An increased number of no-flow capillaries have been described in different diseases and a positive correlation between capillaries with no-flow and high mortality has been shown. All capillaries in patient E2 had flow category 0 or 1, fifty percent in each category. Interestingly the patient at that point had biochemical markers indicating disseminated intravascular coagulation (DIC).

3.1.3 Circular Dark Haloes

Dark haloes were found in two of the patients who died on ECMO (E2 and E4), with the halo edges 12±1 microns from the capillaries. In E2 numerous haloes were present, prominently around capillaries with "no flow". E4 had fewer haloes, and they were also seen surrounding perfused capillaries. The cause of these haloes is uncertain, but one possibility is that they represent precipitated proteins or erythrocyte degradation products leaking from injured capillaries. Another possibility is that they are caused by pericapillary oedema.

3.1.4 Peripapillary Bleedings

Bleeding capillaries have been described in patients with von Willebrand disease, in patients with critical lower limb ischemia, in patients with connective tissue disorders and in patients on anticoagulants. We have reported pericapillary bleedings in the tongue of septic pigs four hours after injection of N. meningitides antigen. Pericapillary bleedings was found in several skin locations of patient E1 (died on ECMO). This patient suffered from systemic lupus erythematosus. He had not been treated with anticoagulants. No macroscopic bleedings could be detected. Capillary erythrocyte leakage is the result of severe damage to the capillary wall and increased fluid leak and oedema would be expected. Patient E1 gained 30 kilos body weight during the first 24 hours on ECMO, and gained another 12 kilos between the first and second measurement.

3.2 Laser Doppler Perfusion Measurements

The major part of skin perfusion takes place in the deeper thermoregulatory plexuses where perfusion is mainly regulated by sympathetic activity. Since perfusion in these plexuses mainly serve a thermoregulatory function, skin nutrition can not be assessed by the LDPM technique. Even though the two patients that died on ECMO (E1 and E4) had the lowest perfusion values of all in both locations and measuring periods, no significant differences were demonstrated du to small numbers and large data variation.

3.3 Limitations

The number of included patients is small and represents a heterogeneous group with acute heart failure, while the reference data were collected from healthy young male students. Since capillary erythrocyte velocities in healthy subjects are not age dependent, we assume that our control group of young students can be used.

3.4 Possible Implications of the Findings

In USA, 40% of the Medicare expenditures occurred in the last month of life and inpatient expenses accounted for over 70% of the decedents' total costs. This indicates increased use of high-tech intensive care facilities when approaching the end of the patients' lives, without gaining much improvement of life expectancy. ECMO and other circulation assist devices are costly in use. Generally accepted criteria for selection of patients for such treatment are missing. Assist devices improve central hemodynamics, but often without improving life expectancy. It is therefore a strong need for diagnostic techniques that can be used to select patients for expensive extracorporeal life support techniques, for estimation of prognosis early after establishing such treatment and to assess the effects of supportive treatment during the use of an assist device.

The idea that the microscopic examination of sublingual microcirculation may serve as a prognostic indicator of critically ill patients with sepsis or cardiogenic shock seems to be accepted. In a study on 68 patients with cardiogenic shock, reduced sublingual functional capillary density was associated with development of organ failure.

A case report on one patient on ECMO examined sublingually by a microscopic method (OPS) showed that capillary flow velocity varied with varying ECMO flow. The changes were most prominent in the smallest capillaries. The small sublingual capillaries correspond to the size of the nutritive skin papillary capillaries examined in our study.

Our study indicates that techniques for bedside assessments of skin microcirculation can be developed to valuable clinical tools for improved handling of patients on assist devises.

4 Conclusion

Microvascular examinations of skin nutritive capillaries in patients on ECMO show major structural and functional pathology in patients dying on ECMO, while patients surviving ECMO have results similar to healthy controls. The finding of intact skin microcirculatory morphology and function in survivors early after establishment of ECMO appears to be a robust and clinically useful finding implying a good prognosis. Pericapillary bleedings or dark haloes, micro-thrombi/capillaries with "no flow", low capillary flow velocity and low functional capillary density are associated with poor prognosis.

Annex—Tables

TABLE 1

Clinical information and outcome for all study patients.

| Patient | Gender | Risk factors | Indication and type of surgery | Indication for ECMO | ECMO duration | Outcome |
|---|---|---|---|---|---|---|
| E1 | Male | SLE chronic kidney graft rejection | Aortic and mitral stenosis. AVR and MVR | Post-cardiotomy shock | 11 days | Death on ECMO |
| E2 | Male | NYHA III EF: 15-20% | Type A aortic dissection. Aortic graft | Post- cardiotomy shock | 2.5 days | Death on ECMO |
| E3 | Male | Previous AMI and lung embolism. Redo | Type A aortic dissection. Aortic graft | Post- cardiotomy shock | 4 days | Death 51 days post operative |
| E4 | Female | Leyden mutation Oral contraceptives | Shock due to massive lung embolism | Cardiogenic shock | 5 hours | Death on ECMO |
| E5 | Male | Pre operative cardiogeneic shock with recent AMI | Mitral insufficiency and CAD MVR + CABG | Post- cardiotomy shock | 3 days | Death 8 hours post ECMO |
| E6 | Male | Reduced EF Heavy smoker | Cardiogenic shock following failed PCI CABG | Post- cardiotomy shock | 7 days | Long-term survivor |
| E7 | Female | Previous cerebral stroke. Re-do after AVR 3 years previously | Mitral endocarditis. Cardiotomy and deposit removal | Post- cardiotomy shock | 4 days | Long-term survivor |
| E8 | Male | DM Type II Cerebral stroke Pulmonary hypertension | Type A aortic dissection. Aortic graft | Post- cardiotomy shock. | 4 days | Long-term survivor |

TABLE 2

Clinical and laboratory data in the ECMO patients at the time of the first microvascular measurement.

| | Group 1 (N = 3) | Group 2 (N = 5) | |
|---|---|---|---|
| Hemoglobin (g/dl) | 9.3 (7.8-10) | 10.1 (9.5-11.2) | NS |
| Erythrocytes transfusions (no. of units) | 21 (10.0-37) | 16.4 (10.0-20) | NS |
| Heart rate (beats/minute) | 74 (68-80) | 82 (55-107) | NS |
| MAP (mm Hg) | 53 (45-63) | 53 (45-60) | NS |
| CVP (mm Hg) | 19 (13.0-28) | 10 (8-18) | NS |
| ECMO (in liters/minute) | 3.5 (3-4) | 4.1 (3.5-4.5) | NS |
| Intra Aortic Balloon Pump? | 2 of 3 | 4 of 5 | NS |
| Vasoactive medication? | 3 of 3 | 3 of 5 | NS |
| $FiO_2$ | 0.68 (0.45-1.00) | 0.60 (0.5-0.7) | NS |
| $SaO_2$ (in percent) | 86 (61-99) | 98 (98-99) | NS |
| $SvO_2$ (in percent) | 70 (70 and 70) | 65.4 (55-72) | NS |
| Lactate (mmol/l) | 5.5 (1.2-12.5) | 3 (1.3-3.6) | NS |
| pH | 7.34 (7.23-7.41) | 7.42 (7.36-7.45) | NS |
| $pCO_2$ (in kPa) | 5.0 (4.7-5.4) | 4.8 (4.4-5.5) | NS |
| Base excess | −4.3 (−12.2-(+0.3)) | −0.6 (−3-(3.5)) | NS |
| Temperature (in ° C.) | 36.8 (36.5-37) | 37.1 (36.9-37.5) | NS |
| CRP (mg/l) | 77.3 (22.0-140.0) | 86.5 (22.0-173) | NS |
| WBC ($10^9$ cells/liter) | 14 (12.0-16.0) | 7.2 (5.0-12.5) | P = 0.02 |
| Urinary output (ml/hour) | 3 (0-10) | 48 (0-100) | NS |
| Dialysis (numbers of patients) | 2 of 3 | 1 of 5 | NS |
| Cumulative positive fluid balance (in liters) | 21 (8-30) | 16.6 (10-26) | NS |

EXAMPLE 2

1. Material and Methods 1.1. Study Population

During a six month period twenty-five healthy term newborns of Caucasian race with healthy mothers were enrolled within the first twenty-four hours after delivery (Table 3).

TABLE 3

Demographic data of the study population (n = 25)

| Values | Mean (range) |
|---|---|
| Gestational age (weeks) | 40.3 (38.3-42.6) |
| Birth length (cm) | 50.0 (48.0-56.0) |
| Head circumference (cm) | 35.0 (32.0-38.0) |
| Birth weight (gram) | 3425 (2946-4536) |
| Apgar scores at 1 min | 9 (7-10) |
| Apgar score at 5 min | 9 (8-10) |
| Male gender (%) | 48 |
| Age at first measurement (hours) | 15 (4-23) |
| Mothers age (years) | 31.8 (20.0-40.0) |

1.2. Microvascular Techniques 1.2.1. Computer Assisted Video Microscopy (CAVM)

In vivo studies of microvascular morphology and physiology were performed by use of a hand-held digital video-microscope (Optilia, D1, Sundbyberg, Sweden) with enlargement 250×, resolution 640×480 pixels and frame rate 15 frames per second. Film sequences were projected and stored on a computer (Mac OS X, QuickTime Player). Five to seven film sequences were taken from each skin area the first three days of life. A high quality frame from each film sequence was used for analysis of capillary density and heterogeneity of distribution of capillaries within the region of interest (ROI). The frames were analyzed off-line in a quantitative way where three equidistant horizontal and three equidistant vertical lines were drawn. The software Xscope (the Iconfactory, Greensboro, N.C., USA) was used for creating the grids. Functional capillary density (FCD) was calculated as the number of microvessels crossing a grid of lines/mm line (c/mm) (De Backer et al., Am. J Respir Crit Care Med, 2002, 166(1) pp. 98-104).

For analyses of inter-observer reliability of the FCD assessments, results were compared from two independent researchers (SF,TW) who blindly assessed visually judged good quality films of eight infants. For examination of the intra-observer reliability, one researcher (SF) performed the same analyses twice several months apart.

Individual capillary flow patterns were analyzed in eight infants with film sequences validated as particularly good. The five best ten-second sequences with no or limited movement artefacts were selected. One experienced researcher performed the analyses (TW). The flow velocity in individual capillaries was scored in a semi quantitative five categories scale (Table 4).

TABLE 4

Flow categories with description of flow in each category.

| Flow Category | Description of flow |
|---|---|
| 0-No flow | Erythrocytes visible, no movement |
| 1-Sluggish flow | Slow cell movement, sometimes backward flow |
| 2-Continuous low flow | Continuous forward movement, mostly slowly |
| 3-Continuous high flow | Continuous forward movement, mostly rapid |
| 4-Brisk flow | Rapidly moving cells throughout the entire film sequence |

Data was expressed as the fraction of capillaries (Fr) in a particular flow category (number of capillaries in this category/total number of counted capillaries). Mean capillary flow-categorical velocity (MFCV) was calculated according to the formula: Fr $(1) \times 1 + $ Fr $(2) \times 2 + $ Fr $(3) \times 3 + $ Fr $(4) \times 4$ (Wester et al. Clin Physiol Funct Imaging 31, 2011, pp 151-8).

1.2.2. Laser Doppler Perfusion Measurements (LDPM)

Microvascular perfusion was assessed with a Moor Blood Flow Monitor (MBF 3D) with Moorsoft (Both Moor instruments, Axminster, Devon, England) for recordings and analyses. The output was given in a semi quantitative scale of flux (arbitrary unit, AU) defined as the product of the number of moving blood cells and their mean velocity in the measured volume (approximately 1 mm$^3$). Seven ten-second sequences with no or limited movement artifacts were taken from each ROI.

1.2.3. Diffuse Reflectance Spectroscopy (DRS)

For measurement of microvascular oxygen saturation, a setup consisting of a spectrometer operating in the visible wavelength region (S2000, Avantes, The Netherlands) and a tungsten halogen light source (AvaLight-HAL, The Netherlands) having an effective spectral range of 450 to 800 nm was used. A polytetrafluoretylene tile (WS-2, Avantes, Netherland) enclosed in a black plastic housing was used as reference. A custom-built fiber optic probe was used for measurements with a fiber composition of three adjacent illuminating fibers (fiber diameter 400μm) and one receiving fiber (fiber diameter 400μm) resulting in an emitting-receiving distance for the probe of approximately 800μm (Meglinsky et al. Med Biol Eng Comput, 2001. 39(1): pp. 44-50). Twelve spectra were collected from each ROI in 20 neonates.

Analyses of the spectra were done by adapting a tissue model based on a diffusion approximation (Farrell et al., Med Phys, 1992. 19(4): pp. 879-88; Jacques, IEEE Transactions on Bio-Medical Engineering, 1989. 36(12): pp. 1 155-1 161). The model included the chromophores melanin, hemoglobin derivatives, water and a Mie and Rayleigh scattering factor. Decomposition of the spectral signature was done by a least square fit of the model to the measured spectra. The decomposition of reflected light spectra was then used to estimate the apparent content of oxy- and deoxy-hemoglobin. Microvascular oxygen saturation was compared with arterial oxygen saturation to estimate oxygen extraction.

1.2.4. Pulse Oxymetry

The arterial oxygen saturation was measured using a pulse oxymeter (Masimo Set, Rad-5v, Irvine, USA) with the probe located on the right hand.

1.2.5. Skin Temperature Measurements

Skin temperature was measured using a surface temperature scanner (Omega Medical, Model no. STS-101-C, USA) attached to the ROI just before measurements with the microvascular techniques. Axillary temperature was taken with an ordinary thermometer (Digitemp, Microlife Asia, Mt1671, Taiwan).

1.2.6. Bilirubin Measurements

A transcutaneous bilimeter (Drager, J M 103, Drager medical, Lubeck, Made in Japan) was used to estimate bilirubin values, a factor in the DRS analysing algorithm.

1.3. Measuring Procedure

To make recordings possible, it was important to have a quiet and satisfied baby. Recordings were made in a room with stable temperature around 21° C. and dimmed light. The baby was lying in its bed. CAVM, LDF and DRS were all recorded at postnatal day one, two and three. The two same researchers conducted all measurements (SF, EH). Two skin regions were defined (ROI): The skin in the centre of the dorsal side of the left hand (H) and the skin in the chest in the midline between the jugulum and left mammilla (C). During examinations the sequence of recordings were always CAVM, followed by LDF and finally DRS measurements. The chest was examined first. Oxygen saturation and skin temperature were recorded before each new technique was applied. Finally axillary temperature and transcutaneous bilirubin were measured. Baby oil (Natusan) was used as immersion oil for the video-microscope. All equipment was gently applied on the skin surface.

1.4. Ethics

Written parental consent was obtained. The study was approved by the Regional Committee for Medical and Health Research Ethics, South-Eastern Norway and by the Scientific Committee of the Hospital.

1.5. Statistics

Demographic data are presented as mean with range. All other variables are reported as mean with standard deviation (SD). For continuous variables, paired t-test was conducted to compare means. P-value<0.05 was considered significant.

Intra-class correlation coefficient (ICC) and Bland-Altman plot were used to analyze test-retest reliability of continuous variables. The heterogeneity was expressed as the coefficient of variation (CoV=SD/mean). Statistical analyses were performed using SPSS for Windows (Statistical Package for the Social Sciences, version 18.0 SPSS Inc., Chicago, Ill., USA).

2. Results

It was possible to obtain data with the three noninvasive techniques in a non-traumatic way during a time period of 30 to 45 minutes with parents present in a standard patient room. Seventeen complete data sets with all three methods were obtained. Spectroscopic examinations were not performed in the first five infants due to technical problems at the start of the study. Three infants were lost for follow up on day two and/or three due to early discharge from the maternity ward.

2.1. Computer Assisted Video Microscopy

Functional capillary density (FCD) was significantly higher in the hand compared to the chest all three days (Table 5).

TABLE 5

Functional capillary density (capillary crossings per mm line) (n = 25).

| | Day | | | |
|---|---|---|---|---|
| | 1 | 2 | 3 | p-value (day 1 versus day 3) |
| Chest (C) | 11.3 (1.5) | 11.0 (1.7) | 10.7 (1.6) | p = 0.14 |
| Hand (H) | 13.2 (2.0) | 13.2 (1.9) | 12.4 (1.6) | p = 0.05 |
| p-value | p < 0.001 | p < 0.001 | p < 0.001 | |

Data given as mean (SD)

There was a slight tendency towards a reduction in the number of FCD both in chest and hand from day one to three. The heterogeneity of FCD expressed as CoV of five repeated measurements was 11-13%.

2.1.1. Test-Retest Reliability of FCD

Intra-observer reliability of the prime investigator (SF) was high (ICC 0.72 (0.54-0.83)), although there was a difference in mean scores (11.5 versus 10.7 c/mm, p<0.001). When the second set of FCD values from SF was compared with data from the more experienced researcher (TW) the mean FCD scores were similar (10.7 versus 10.8 c/mm, p=0.70). Inter-observer reliability was also good (ICC 0.54 (0.31-0.72)). The Bland-Altman plots, both for inter- and intra-observer tests, showed increased difference between the two data sets with increasingly capillary density (FIGS. 3a and b).

2.1.2. Capillary Flow Patterns

The dominant capillary flow category was category three (continuous high flow), but flow category two (continuous low flow) was also represented (Table 2, FIGS. 4a and b). Flow categories zero (no flow) and four (brisk flow) were not found. The mean flow-categorical velocity (MFCV) was similar both in the chest and hand at all the three days, varying between 2.57 (0.10) and 2.71 (0.11).

2.2. Laser Doppler Perfusion Measurements

The skin laser Doppler perfusion was significantly higher in the chest compared with the hand (Table 6).

TABLE 6

Laser Doppler perfusion (AU) (n = 25).

| | Day | | | |
|---|---|---|---|---|
| | 1 | 2 | 3 | p-value (day 1 versus day 3) |
| Chest (C) | 109.1 (26.0) | 101.4 (24.6) | 100.8 (25.3) | p = 0.62 |
| Hand (H) | 58.9 (17.5) | 54.3 (15.8) | 46.9 (14.8) | p = 0.09 |
| p-value | p < 0.001 | p < 0.001 | p < 0.001 | |

Data given as mean (SD)

There was a non-significant trend towards a reduction in skin laser Doppler perfusion from day one to three both in chest and hand. The heterogeneity of perfusion expressed as CoV in seven repeated measurements at three consecutive days was 24-32%.

2.3. Diffuse Reflectance Spectroscopy

The oxygen saturation of microvascular erythrocytes ($SmvO_2$) was significantly higher in the chest compared to the hand all three days (Table 7) with no changes over time.

TABLE 7

Microvascular oxygen saturation ($SmvO_2$) (%) (n = 20)

| | Day | | | |
|---|---|---|---|---|
| | 1 | 2 | 3 | p-value (day 1 versus day 3) |
| Chest (C) | 88.1 (5.2) | 87.8 (10.0) | 86.7 (9.0) | P = 0.07 |
| Hand (H) | 79.9 (15.2) | 82.7 (11.8) | 82.2 (12.1) | P = 0.77 |
| p-value | p < 0.05 | p < 0.05 | p < 0.05 | |

Data given as mean (SD)

The heterogeneity of twelve repeated DRS measurements, expressed as CoV, was 9-18%.

Oxygen extraction defined as $SaO_2$ minus $SmvO_2$, showed significant difference between chest and hand with higher oxygen extraction in the hand on all three days (mean (SD)); Chest day 1-3: 14.5 (1.6), 14.1 (3.1), 11.7 (2.7); Hand day 1-3: 23.5 (3.4), 20.2 (2.8), 24.3 (3.5), There were no changes with time.

2.4. Other Results

As expected, bilirubin levels increased from day one to three. Temperature, pulse and arterial oxygen saturation were stable all three days, without differences between the sexes (data not shown).

3. Discussion

It was possible to obtain reproducible non-invasive skin microvascular data in a non-traumatic way in healthy term newborns using Computer Assisted Video Microscopy, Laser Doppler Perfusion Measurements and Diffuse Reflectance Spectroscopy.

3.1. The Model

The cardio-pulmonary adaptation in neonates with closure of the fetal shunts mainly occurs during the first hours of life, but is not completed until days to months after birth. Other adaptive responses such as reduction of total body water accompanied by 4-7% weight loss, hemolysis of fetal erythrocytes and production of erythrocytes with adult hemoglobin, occurs during the first days to weeks. The hematocrit peaks at two hours of age and then decreases steadily over the next weeks. Our neonates were examined the first, second and third day of life when many of these adaptive processes affecting the central hemodynamics and hemorheology, and thereby microvascular perfusion, occur.

3.2. CAVM 3.2.1. Microvascular Anatomy

Our newborns were not sedated and spontaneous movements sometimes reduced quality of recordings. Training was required to record high quality film sequences. In adult skin microvessels are arranged into superficial papillary nutritive capillaries ensuring the metabolic need for epithelial proliferation, and a deep and a superficial horizontal plexus mainly serving body thermoregulation. In adult hands and feet, the regions with the most differentiated structure, the superficial nutritive capillaries are seen as "dots" or "comma shapes" in the microscope. The newborn epithelium is thinner than in adults and the vascular architecture is not fully differentiated. With the microscope a disorderly network with horizontal microvessels were seen.

Functional capillary density assessments were therefore assessed as number of microvessels crossing a grid of lines per mm line (c/mm).

3.2.2. Functional Capillary Density (FCD)

Oxygen has a limited capacity for diffusion in biological tissues, in contrast to the diffusion capacity for $CO_2$. August Krogh, the Nobel Prize winner in Physiology or Medicine in 1920, postulated that all cells need to be located within a critical cylinder of a perfused capillary to get sufficient oxygen supply. Within this cylinder the oxygen availability falls exponentially with increasing distance from the centre of the capillary. Cells outside such cylinders will experience lack of oxygen delivery independent of the erythrocyte oxygen saturation in the nearest capillary. This means that FCD and heterogeneity of microvessels have to be within defined limits to ensure nutrition and oxygen availability to all cells in a tissue.

3.2.3. FCD Values

In the chest FCD varied between 10.7 and 11.3 c/mm, and in the hand between 12.7 and 13.2 c/mm, significantly higher in the hand compared to the chest on all three days (Table 3). There was also a clear tendency towards reduction in FCD from day one to day three for both locations.

3.2.4. Heterogeneity of Microvessels

An uneven distribution of perfused capillaries may give low oxygen tension to some cells in spite of a normal $SaO_2$. The heterogeneity of FCD expressed as CoV in five repeated measurements was 11-13%. Healthy adults measured in fossa Tabatiere (CoV: 15-30%) had values in the same range.

3.2.5. Capillary Flow Patterns

In our healthy newborns the dominant microvessels flow categories were flow category three (60-70%) and flow category two (25-35%) (table 2, FIG. 4). Flow categories zero and four were not seen. The velocities were similar in the chest and the hand all three days. We have previously found similar flow categories in the skin (Fossa Tabatiere) of healthy young adult controls (75% of skin microvessels were in flow category three, 25% in category two) using the same equipment and the same examiners.

The mean capillary flow-categorical velocity (MFCV) was similar in the chest and the hand with little variation on the consecutive days (varying between 2.57 and 2.71). MFCV in the newborns were also similar to what we previously found in the healthy young adults in the skin of Fossa Tabatiere (2.56-2.88),

3.2.6. Reproducibility

Reproducibility analyzes were performed by one experienced investigator (TW) and one less experienced at the start of the study (SF). The inter-observer variation in FCD was small when the second set of results from SF was compared with the results of TW (FIG. 2a). The intra-observer reliability test from SF showed a statistically significant decrease in mean FCD values from the first to the second analysis done several months apart, probably due to the effect of the learning curve (FIG. 2b), indicating the need for a training program for frame and film analysis to obtain reproducible results.

3.2.7. OPS/SDF Versus CAVM

Human intra-vital microvascular microscopy has been performed for many years. For more than 10 years OPS (Orthogonal Polarization Spectral Imaging) and SDF (Sidestream dark field imaging) have been used. These systems consist of polarized green light (wavelength 550 nm) and a filtration system to visualize the microcirculation. The light is absorbed by hemoglobin and red blood cells therefore appear dark. The systems can, however, only be used on mucous membranes (the tongue), and on some areas with thin skin in human newborns. In contrast CAVM uses white light, which gives pictures in colors and the possibility to examine different skin types.

3.3. LDPM

The laser Doppler principle for quantifying microvascular perfusion in tissue volumes in the range of 1 $mm^3$, has been commercially available for nearly 40 years, but the technique has hardly any routine applications in clinical medicine. This is partly explained by the fact that the method assesses a mix of both superficial papillary capillaries, mainly serving the nutritive perfusion, and deeper plexuses, mainly serving the thermoregulatory function.

In this study perfusion in the chest skin was significantly higher as compared to the hand, corresponding to a higher temperature in the chest (+2.8° C.) (Table 4). The heterogeneity of repeated measurements expressed as CoV was 24-32%, considerably higher than for the CAVM and DRS data.

3.4. DRS

3.4.1. The DRS Method

Diffuse Reflectance Spectroscopy was used to assess the oxygen saturation of erythrocytes in the microcirculation ($SmvO_2$). The measuring volume of DRS is dependent on the emitting light spectrum, the optical properties of the tissue and the design of the measuring probe. The equipment used in this study is estimated to have a measuring volume of <1 $mm^3$ corresponding to a measuring depth of approximately 0.8 mm in skin (Meglinsky et al., supra).

3.4.2. DRS Results

Microvascular oxygen saturation ($SmvO_2$) represents the balance between oxygen supply and consumption in the measuring volume. The supply is again dependent on the product of perfusion and arterial oxygen saturation, while the consumption is dependent on the metabolic rate of the tissue. Since $SaO_2$ in our newborns was near to 100%, our $SvmO_2$ data showed extraction between 12 and 20%. In the newborns both thermoregulatory and nutritive perfusion takes place in the DRS measuring volume in contrast to in adult skin where only the papillary nutritive perfusion is assessed. Parts of the perfusion in the measuring volume in the newborn may also have a transport function (the horizontal structure in newborns as compared with the vertical papillary loops in the DRS measuring volumes of adult skin).

Higher $SmvO_2$ in the chest (86-88%) compared to the hand (76-80%) may reflect the differences in the microvascular architecture, but also the lower perfusion in the hand as demonstrated by the LDPM. The lower perfusion in the hand with a compensatory higher oxygen extraction may also be a way of preventing unnecessary loss of heat.

4. Conclusion

It is believed that microscopy and spectroscopy, together, are the most useful techniques for assessing skin microcirculation in neonates. They both have measuring volumes of fractions of 1 $mm^3$ and a resolution corresponding to individual microvessels. Small measuring volumes give high resolution, but at the price of a larger variation in measured values, i.e. a larger spread in repeated measurements. This problem can be handled by using the mean of repeated measurements to express an average value from a tissue, and the spread of repeated measurements can be used to describe the heterogeneity of the microcirculation.

All cells are dependent on delivery of nutrients and oxygen from the microcirculation, but assessments of microvascular function are not done in routine clinical practise. In this study we have shown that it is feasible to obtain reproducible information from the skin microvasculature in newborns. The techniques used in this study gives information on the quality of delivery of oxygen for the metabolic process necessary for growth and development.

EXAMPLE 3

Erythromelalgia and Microcirculation

Erythromelalgia (EM) is a clinical syndrome characterized by erythema, increased skin temperature and burning pain in the extremities. The pain is relieved by cooling and aggravated by warming. EM is commonly divided into primary and secondary cases, depending on whether or not there is an underlying disease. Symptoms vary from mild discomfort to limbs threatening hypoxia and amputation.

The pathogenesis of EM is debated. The inventor and others have proposed a hypothesis of a common final pathway of the pathogenesis: maldistribution of skin microvascular perfusion through anatomical or functional microvascular arteriovenous shunts, with increased thermoregulatory perfusion and a relative lack of nutritive capillary perfusion in affected skin. The tissue consequently becomes hypoxic, causing supplying arterioles to dilate, leading to a paradoxical situation with coexistence of hyperaemia and hypoxia. This hypothesis gives an explanation for why cooling universally reduces pain. The cooling reduces metabolism, and thereby the hypoxia; the improvement of tissue oxygenation reduces the arteriolar dilatation, and hyperaemia is less pronounced: the vicious cycle is reversed.

The study described below utilises the 6 parameters of the invention as described herein to investigate erythromelalgia, an example of localised circulatory failure.
Material and Methods
Material Our group has gathered a group of 207 patients, the largest seen by a single group or institution in the Western world.
Methods
Computer Assisted Video Microscopy (CAVM).

This technique involves a hand held video-microscope applied gently on the surface of the region of interest. Pictures or film sequences are projected and stored on a computer. A digital video microscope (Optilia, D1, Sundbyberg, Sweden) with enlargement 250×, resolution 640× 480 and frame rate 15 fps (frames per second) is used. An analogue to digital converter (Canopus, Kobe, Japan) is used to project and store the film sequences on a Mac Book pro, using the software iMovie (all Apple, Cupertino, USA).

Five to seven recordings are taken from each site. We select the five best 10 seconds sequences with no or limited movement artefacts. These sequences are being analyzed in a semi quantitative way; three equidistant horizontal and three equidistant vertical lines were drawn. The software Xscope (the Iconfactory, Greensboro, N.C., USA) is used for creating the grids. Vessel density (FCD) is calculated as the number of vessels crossing these lines divided by the total length of the lines. In each patient, the data from the five best records are averaged. Heterogeneity of FCD is expressed as the coefficient of variation (CoV=SD/mean) of the density of capillaries in the five film sequences.

The red blood cells' flow pattern in the capillaries varies over time. For analysis, the flow velocity of each capillary of the five film sequences are visually scored into one of five groups from "no flow" to "brisk flow" and expressed as mean flow velocity and fraction of capillaries in each flow category (n=10). The heterogeneity of the mean flow values is expressed as CoV (Wester et al., supra).
Diffuse Reflectance Spectroscopy (DRS).

A spectrometric set-up is used with a spectrometer operating in the visible wavelength region (S2000, Avantes, Netherland) and a tungsten halogen light source (AvaLight-HAL, Netherland) having an effective spectral range of 450 to 800 nm. A polytetrafluoretylene tile (WS-2, Avantes, Netherland) enclosed in a black plastic housing was used as reference. A custom-built fiber optic probe is used for measurements with a fiber composition of three adjacent illuminating fibers (E 400μηη) and a receiving fiber (E 400μηη) resulting in an emitting-receiving distance for the probe of approximately 800μηη (Meglinsky I et al. supra). Twelve records are taken from each region. Spectral analysis are done by adapting a tissue model based on a diffusion approximation (Farrell J, et al. supra). The model included the chromophores melanin, hemoglobin derivatives (Zijlistra W G, et al. Visible and Near Infrared Absorption Spectra of Human and Animal Haemoglobin: Determination and Application: Brill Academic Publishers; 2000), water (Hale G M, et al. Appl Opt. 1973; 12:555-63) and a scattering factor accounting for both Mie and Rayleigh components. Decomposition of the spectral signature is made by a least square fit of the model to the measured spectra. The decomposition of reflected light spectra is then used to estimate the apparent content of oxy- and deoxyhemoglobin.
Patient Protocol Shown in FIG. 10.

Normal medications are allowed. Acetylic salicylic acid acid is discontinued one week before the examinations and misoprostol is optimally discontinued for 4 weeks.

A maximum of 225 minutes will be allowed to complete the examinations.
  1. The patient is welcomed, and anamnestic data are rechecked. Severity score during the last week and the last month will be evaluated. Menstrual cycle may influence the vascular function and is therefore recorded.
     It will be noted if fertile patients use oral contraceptive pills. Outside temperature is recorded.
  2. The subject rests in a supine position for 15 min in a room with an ambient temperature of 23±1° C. protected from physical and psychological stress. The test extremity is stabilized with soft pillows to avoid gross movement artefacts.
  3. Clinical assessments are recorded:
     VAS (visual analogue scale) score
     Skin colour/photo documentation
  4. Baseline parameters are recorded:
     Skin temperature is measured on the pulp of the first toe on the left foot.
     Baseline DRS will be recorded at the pulpa and between the $1^{st}$ and $2^{nd}$ toe/finger. Eight 10-second sequences will be recorded.
     Baseline CAVM will be recorded on the terminal phalanx of the first toe, just proximal to the nail bed where the capillary loops are perpendicular to the skin surface. An alternative site is the arch of the foot containing fewer AV anastomoses. Approximately 20-second sequences of film and 8 frames (to determine capillary density and heterogeneity) are recorded.
  5. The subject is heated according to the core body heating procedure (Mork C et al. J Invest Dermatol. 2004 March; 122(3):587-93)
  6. Step 4 is repeated.
  7. Skin needle biopsies are taken from the foot arch, and stored in deep freezer.

8. Blood samples for haematological examination and for genetic testing will be collected.

We believe that microvascular arterio-venous shunting in affected skin leads to tissue hypoxia and secondary compensatory hyperperfusion.

EXAMPLE 4

Skin Microvascular Assessments to Provide a Prognosis in a Patient with Traumatic Limb Ischemia Acute traumatic limb ischemia is a challenge for trauma surgeons. Is the life and function of the limb salvageable or has the period of ischemia given irreversible tissue damage? The surgeons may have to make quick decisions being aware that wrong decisions may cause either amputation of a savable limb or development of necrosis and sepsis in a non-savable limb where a salvage procedure was tried. In the worst case the latter may contribute to a fatal outcome in a multi-traumatized patient. Currently surgeons lack predictors for limb prognosis. A way of monitoring the circulation of a re-perfused limb is therefore of great importance.

To monitor these patients, clinical tests/signs like capillary refill time, skin temperature and skin color together with arterial blood pressure measurements are mainly used to evaluate the circulation of affected limbs. Blood tests like lactate, creatine kinase (CK) white blood cell count (WBC) and C-reactive protein may also be helpful, but none of these tests/signs are particularly reliable in predicting outcome in reperfused limbs.

Materials and Methods:
The Patient

A 33 year old female patient was involved in a high-energy car crash. At the site of injury she could move the fingers of the injured arm and has maintained intact sensory function. She had a moderate severe brain concussion corresponding to a Glasgow Coma scale of 12, sixty minutes after the initial injury. She arrived at our hospital (a level I trauma center), nearly 120 minutes after the accident and was examined according to guidelines for advanced trauma and life support (ATLS).

At hospital admittance, the left upper extremity was cold, pale and had no palpable pulse. X-ray showed a humerus shaft fracture, an elbow fracture with luxation, a proximal ulnar fracture and a distal antebrachi fracture. In addition CT showed an occluded left subclavian artery. Injury to the descending thoracic aorta Aortic was also shown, but this injury was not in need of repair.

An axillo-brachial bypass with autologous vein and an embolectomia was done to reperfuse the arm. Arterial flow to the arm was re-established 250 minutes after the injury. The fractures were initially fixed with an external fixator. Prophylactic fasciotomy was done in the limb's entire length. At the operating theatre, the ulnar and median nerves were visualized without signs of injury After the embolectomia and by-pass procedure, the flow in the brachial artery was 180 millilitres per minute, the left hand was warm and had capillary re-fill time of two seconds.

Microvascular Measurements

Computer assisted video microscope (CAVM) and diffuse reflectance spectroscopy (DRS) were used. The first microvascular examinations were performed only a few hours after reperfusion surgery on the day of admittance (Day 0), and repeated on days 1, 2, 5 and 9. The skin on the dorsum of the hand, between the first and second metacarpus (fossa Tabatie're) was examined by CAVM and DRS. And each time repeated measurements were performed. Measurements of the uninjured hand served as a control. The time delay between examinations of the same monitoring modality on the two hands was only a few minutes.

Computer Assisted Video Microscopy (CAVM)

A hand-held digital microscope (Mediscope, OP-120 01 1), (Optilia Instruments AB Sollentuna, Sweden) with a 200× magnifying lens, a resolution 640×480 and frame rate of 15 frames per second was used. The use of the microscope and analysis of parameters is described elsewhere.

CAVM parameters of interest are functional capillary density (FCD), heterogeneity of FCD, microvascular flow-patterns and pericapillary pathology. CAVM films were analyzed blindly by an experienced investigator and also by the software Java Cap (Eye catcher technologies, Linkoping, Sweden). Baby oil (Natusan) was used as immersion oil for the video-microscope. All equipment was gently applied on the skin surface.

Diffuse Reflectance Spectroscopy (DRS)

For measurement of microvascular oxygen saturation, a spectrometric setup consisting of a spectrometer operating in the visible wavelength region (S2000, Avantes, The Netherlands) and a tungsten halogen light source (AvaLight-HAL, The Netherlands) was used. The setup has an effective spectral range of 450 to 800 nm. A polytetrafluoretylene tile (WS-2, Avantes, Netherland) enclosed in a black plastic housing was used as reference. A custom-built fiber optic probe was used for measurements with a fiber composition of three adjacent illuminating fibers (fiber diameter 400µm) and one receiving fiber (fiber diameter 400µm) resulting in an emitting-receiving distance for the probe of approximately 800µm. The estimated measuring volume of the equipment has been estimated to be in the range of 0.1 mm$^3$. Seven spectra were collected from each hand at each measurement.

Analyses of the spectra were done as described in Example 3. Microvascular oxygen saturation was compared with arterial oxygen saturation to estimate oxygen extraction.

Data Presentation

The results from one hand were compared to the results from the other hand taken the same day. Results from one hand were also compared to results from the same hand taken another day. A group of eight healthy male students serve as a control group.

Results

Clinical Course from Admittance to Day 13 (Amputation Day).

The patient was treated in the intensive care unit. Except for wounds in her forehead and knee, the only injuries needing surgery were in her left arm. She was hemodynamically stable through the entire course, but received norepinephrine initially to maintain a mean arterial pressure above 70 mm Hg. She did not suffer from lung ventilation problems. She did not develop kidney failure or other organ failures. Attempts were made to wake her up at day 3, but due to confusion and exaggeration she was slept down again. On day 5 she had a fever episode (maximum temp 39.2° C.), but no other signs of infection.

On day 9 she got a fever (maximum temp 39.5° C.), tachycardia (125 beats/minute) and her white cell blood count rose to 16.6×10$^9$ cells/l. However, the concentration of C-reactive protein fell and there was not found other signs of infection. Bacteriologic tests from blood and wounds taken this day were all negative. She stabilized to day 13 when a planned inspection of the split skin graft was done. This operative procedure showed necrotic muscles in the forehand and no pulse distal of elbow. At this time there were no verified information of voluntary movements of the hand or fingers. Sensory function had not been tested The patient was brought back to the theater for an above elbow amputation. From here to discharge 12 days later the patient developed no further complications.

At follow-up three months after hospital discharge all her wounds has healed. She has a left arm with amputation level 20 centimeters below the acromio-clavicular joint.

Computer Assisted Video Microscopy (CAVM) Results

Functional capillary density: On the first measurement, only a few hours after the reperfusion procedure, the functional capillary density was 33 percent lower in the left hand as compared to the opposite side. The next day, this difference had increased to 42 percent. At day five, no difference was seen in FCD between the two hands, neither was there a difference at day 9. The FCD values of both hands after day five were in the same range as for the healthy volunteers in Example 1.

The heterogeneity of the FCD: The coefficient of variation varied between 0.20 and 0.36 on the right arm and between 0.15 and 0.35 on the left side, for both hands the highest value was the day after the accident and reperfusion.

Capillary flow pattern: For all measurements except on the left arm on day 9, an overwhelming majority of capillaries were in category 2 and 3 (continuous flow). The flow pattern and mean-categorial flow index were in the same range as our healthy controls.

No pericapillary pathology or dark haloes were seen at any measurements.

All CAVM parameters are summarized in the table below.

TABLE

CAVM parameters during the observation period. For FCD the measured value from the right hand is 1, while the left hand is the quotient of FCD(Left)/FCD(Right).

| | Right hand | | | Left hand | | |
|---|---|---|---|---|---|---|
| Day | FCD | CoV of FCD | MCFV | FCD | CoV of FCD | MCFV |
| 0 | 1 | 0.26 | 2.50 | 0.67 | 0.29 | 2.62* |
| 1 | 1 | 0.35 | 2.86 | 0.58 | 0.36 | 2.58 |
| 5 | 1 | 0.21 | 2.90 | 1.05 | 0.20 | 2.71 |
| 9 | 1 | 0.22 | 2.73 | 0.96 | 0.15 | 3.64 |

Discussion

In an arm there are five main kinds of tissues: bone, fat, skin, muscle and nervous tissue. The tolerance for hypoxia varies between cells from different tissues, and is related to varying metabolic rate. For a limb to survive and function after an ischemic trauma, a minimum of cells from all kinds of tissues has to survive. In cases with traumatic ischemia the decision whether to amputate or to try limb-salvage surgery may be hard, and is related to the time from ischemia to reperfusion. After reconstructive surgery it is difficult to predict the final functional outcome related to survival of cells in the different tissues, based on clinical examination, or by assessments by transcutaneous oxygen tension measurements, or Laser Doppler perfusion assessments.

In this patient skin, bone and fat tissue survived, muscle tissue partly became necrotic, while nerve tissue lost all function. An early amputation would have been safer for the patient, and resources, including 12 hours of operating time following the initial operation (vascular reconstruction and external fixation), would have been saved.

Our skin microvascular examinations were able to quantify a circulatory insufficiency in the injured arm after the vascular reconstruction, as compared with reference data and data from the uninjured arm. The diagnostic sensitivity of our system is therefore sufficient to discover a nutritional problem. This case indicates that the diagnosed circulatory failure was too severe for nervous tissue to survive (nerve tissue has the highest metabolic demands and the lowest tolerance to hypoxia), the circulatory failure was at a critical level for muscle tissue survival, but was below a critical level for skin survival. Our innovation may be used to guide clinical decision-making on the difficult question of whether to perform an early amputation, or to use time and resources and add a risk of life threatening complications (like sepsis), associated with complicated reconstructions.

EXAMPLE 5

Case Study and Prognosis of a Patient Receiving Ecmo

A 54 year old woman received irradiation treatment against the chest at the age of 16 because of a malignancy. She was successfully treated, but in recent years has experienced progressive chronic heart failure due to complications from the previous irradiation: Aortic valve stenosis, mitral valve stenosis and insufficiency, moderate to severe left ventricular diastolic dysfunction, in addition to moderately reduced pulmonary function. She was operated on with prosthetic replacement of the two valves. During the primary operation she came off cardio-pulmonary bypass and was transferred to the postoperative unit. In the postoperative period she was treated for insufficient heart function with inotropes and Intra-aortic balloon pumping, and with hemodialysis secondary to renal failure. On postoperative day 2 the heart failure became critical and she was connected to an ECMO system. After establishment of ECMO, clinical assessments as well as standard monitoring parameters, (central hemodynamic parameters (pressures and cardiac output), arterial oxygen saturation, blood lactate, acid base balance and cerebral oxygenation assessed with NIRS (Near infrared spectroscopy) were within reference levels, and she was regarded a candidate for heart transplantation (HTx).

After establishment of ECMO, and daily thereafter she was examined according to the present invention by assessment of the 6 microvascular parameters discussed herein, namely:
(a) functional capillary density (FCD);
(b) heterogeneity of the FCD;
(c) capillary flow velocity;
(d) heterogeneity of capillary flow velocity;
(e) oxygen saturation of microvascular erythrocytes ($SmvO_2$); and
(f) heterogeneity of $SmvO_2$.

Clinical course: The patient was treated with veno-arterial ECMO for 10 days. The ECMO was then converted to veno-venous ECMO and the patient died during this circulatory support on day 11. During this course she had multiple surgical revisions due to a bleeding tendency, partly related to the anticoagulation needed for the two mechanical heart valves, partly to a multi-transfusion syndrome with accompanying coagulopathy. The standard monitoring techniques showed acceptable values, and only on day 10 she was taken off the transplant list due lack of clinical progress and development of extensive ulcerations, skin necrosis, on the buttocks and the back. On day 10 the conversion from veno-arterial to veno-venous ECMO was decided because of lack of clinical progress, and ECMO was turned off on day 11, while the heart was still beating due to progression of the skin necrosis on the back and deterioration of central hemodynamic readings, and critical NIRS values indicating irreversible brain damage. The patient died shortly thereafter.

The microvascular data were continually reviewed shortly after collection. The CAVM collected frames and films were scored by two independent and experienced examiners according to the impression of FCD (parameter (a)), heterogeneity of FCD (parameter (b)), CFV (parameter (c)) and heterogeneity of FCV (parameter (d)), and a written report was made. For all the films and frames at all examinations there was total agreement between the two examiners that all parameters showed values outside reference values, and it was concluded that existed a severe circulatory failure in the nutritive skin perfusion.

The DRS data, parameter (e) and (f), are shown in FIGS. 9(a) and (b).

The invention claimed is:

1. A method of identifying or monitoring circulatory failure in a subject using a microscope and a spectrometer for measuring diffuse reflectance, said method comprising:
  (i) applying a microscope emitting white unpolarized light and a light emitting probe connected to the spectrometer to the skin of a subject, and measuring:
    (a) functional capillary density (FCD);
    (b) heterogeneity of the FCD;
    (c) capillary flow velocity;
    (d) heterogeneity of capillary flow velocity;
    (e) oxygen saturation of microvascular erythrocytes ($SmvO_2$); and
    (f) heterogeneity of $SmvO_2$;
  wherein parameters (a) to (d) are measured using white unpolarized light microscopy image(s) yielded by white unpolarized light microscopy, and parameters (e) and (f) are measured by diffuse reflectance spectroscopy (DRS);
  (ii) comparing measurements obtained in respect of parameters (a) to (f) in the subject with measurements of the same parameters in a healthy control; and
  (iii) determining the deviation between the measurements of parameters (a) to (f) in the subject and the healthy control, wherein a statistically significant deviation indicates circulatory failure in said subject; and further comprising the step of ceasing, continuing or altering a therapeutic intervention or regimen based on the outcome of said determination step (iii).

2. The method claim 1, wherein the measurement comprises use of a video light microscope, images obtained therefrom, or a combination thereof.

3. The method of claim 1, wherein one or more of parameters (a) to (d) are measured using computer assisted video microscopy (CAVM), images obtained therefrom, or a combination thereof.

4. A method of making a prognosis for a subject with circulatory failure, the method comprising:
  (i) applying a microscope emitting white unpolarized light and a light emitting probe connected to a spectrometer to the skin of a subject, and measuring:
    (a) functional capillary density (FCD);
    (b) heterogeneity of the FCD;
    (c) capillary flow velocity;
    (d) heterogeneity of capillary flow velocity;
    (e) oxygen saturation of microvascular erythrocytes ($SmvO_2$); and
    (f) heterogeneity of $SmvO_2$;
  wherein parameters (a) to (d) are measured using white unpolarized light microscopy image(s) yielded by white unpolarized light microscopy, and parameters (e) and (f) are measured by diffuse reflectance spectroscopy (DRS);
  (ii) comparing measurements obtained in respect of parameters (a) to (f) in the subject with measurements of the same parameters in a healthy control; and
  (iii) determining the deviation between the measurements of parameters (a) to (f) in the subject and the healthy control, wherein a statistically significant deviation indicates circulatory failure in said subject; and further comprising the step of ceasing, continuing or altering a therapeutic intervention or regimen based on the outcome of said determination step (iii).

5. The method of claim 1, further comprising measurement of oxygen extraction by the microvasculature.

6. The method of claim 1, wherein the subject:
  (i) is being considered for or undergoing intensive care therapy, such as extra-corporeal membrane oxygenation (ECMO) or extra-corporeal life support treatment (ECLS); or
  (ii) is suffering from pre-eclampsia; or
  (iii) is suffering from sepsis; or
  (iv) is suffering from chronic or acute heart failure; or
  (v) has a chronic skin wound; or
  (vi) is asphyxiated; or
  (vii) has acute or chronic respiratory failure; or
  (viii) has acute or chronic limb ischaemia;
  (ix) has had an organ transplant;
  (x) has erythromelalgia.

7. The method of claim 4, further comprising measurement of oxygen extraction by the microvasculature.

8. The method of claim 1, wherein the method is computer implemented.

9. The method of claim 4, wherein the method is computer implemented.

10. The method of claim 4, wherein the subject:
  (i) is being considered for or undergoing intensive care therapy, such as extra-corporeal membrane oxygenation (ECMO) or extra-corporeal life support treatment (ECLS); or
  (ii) is suffering from pre-eclampsia; or
  (iii) is suffering from sepsis; or
  (iv) is suffering from chronic or acute heart failure; or
  (v) has a chronic skin wound; or
  (vi) is asphyxiated; or
  (vii) has acute or chronic respiratory failure; or
  (viii) has acute or chronic limb ischaemia;
  (ix) has had an organ transplant;
  (x) has erythromelalgia.

11. The method of claim 5, further comprising measurement of oxygen extraction by heterogeneity of said extraction.

12. The method of claim 7, further comprising measurement of oxygen extraction by heterogeneity of said extraction.

* * * * *